(12) United States Patent
Yasumoto et al.

(10) Patent No.: US 8,138,159 B2
(45) Date of Patent: Mar. 20, 2012

(54) COMPOSITION FOR INHIBITING FUNCTION OF HUMAN FLT3

(75) Inventors: Masazumi Yasumoto, Kusatsu (JP); Masamitsu Shimada, Otsu (JP); Fumitsugu Hino, Kusatsu (JP); Ikunoshin Kato, Koka (JP)

(73) Assignee: Takara Bio Inc., Otsu-Shi (JP)

( * ) Notice: Subject to any disclaimer, the term of this patent is extended or adjusted under 35 U.S.C. 154(b) by 1716 days.

(21) Appl. No.: 10/574,904

(22) PCT Filed: Oct. 7, 2004

(86) PCT No.: PCT/JP2004/014851
§ 371 (c)(1),
(2), (4) Date: Apr. 6, 2006

(87) PCT Pub. No.: WO2005/035004
PCT Pub. Date: Apr. 21, 2005

(65) Prior Publication Data
US 2011/0105582 A1  May 5, 2011

(30) Foreign Application Priority Data
Oct. 9, 2003  (JP) .................................. 2003-350253

(51) Int. Cl.
*A61K 31/70* (2006.01)
*C07H 21/02* (2006.01)
*C07H 21/04* (2006.01)
*C12Q 1/68* (2006.01)
*C12N 5/00* (2006.01)

(52) U.S. Cl. .... 514/44 A; 435/375; 435/377; 435/320.1; 536/23.1; 536/24.1; 536/24.5

(58) Field of Classification Search ........................ None
See application file for complete search history.

(56) References Cited

U.S. PATENT DOCUMENTS
2007/0031844 A1 * 2/2007 Khvorova et al. ................ 435/6

FOREIGN PATENT DOCUMENTS
WO   WO-00/11470 A1   3/2000
WO   WO-2000/11470 A1  3/2000

OTHER PUBLICATIONS

Rosnet, O. et al., Blood, Aug. 15, 1993, 82(4), pp. 1110-1119.
Yee et al., Blood, Oct. 15, 2002, 100(8), pp. 2941-2949.
Yamamoto et al., Blood, Apr. 15, 2001, 97(8), pp. 2434-2439.
Fire et al., Nature, Feb. 19, 1998, vol. 391, pp. 806-811.
Dykxhoorn et al., Nature Rev. Mol. Cell Biol., Jun. 2003, vol. 4, pp. 457-467.
Elbashir et al., Nature, May 24, 2001, vol. 411, pp. 494-498.
Heidenreich et al., Blood, Apr. 15, 2003, 101(8), pp. 3157-3163.
Martinez et al., Proc. Natl. Acad. Sci. USA, Nov. 12, 2002, vol. 99, pp. 14849-14854.
Wilda et al., Oncogene, 2002, vol. 21, pp. 5716-5724.
Scherr et al., Blood, Feb. 15, 2003, 101(4), pp. 1566-1569.
Wohlbold et al., Blood, Sep. 15, 2003, 102(6), pp. 2236-2239.
Shen et al., FEBS Letters, Mar. 27, 2002, vol. 539, pp. 111-114.
Holt et al., Molecular and Cellular Biology, Feb. 1988, p. 963-973.
Bettinger et al., Current Opinion in Molecular Therapeutics, 2001, 3(2), pp. 116-124.
Verzeletti et al., Human Gene Therapy, Oct. 10, 1998, vol. 9, pp. 2243-2251.
Wierda et al., Seminars in Oncology, Oct. 2000, vol. 27, No. 5, pp. 502-511.
Gewirtz et al., Blood, Aug. 1, 1998, vol. 92, No. 3, pp. 712-736.
Bernstein et al., Nature, Jan. 18, 2001, vol. 409 pp. 363-366.
Tuschl et al., Genes & Dev.1999, vol. 13 pp. 3191-3197.
Zamore et al., Cell, Mar. 31, 2000, vol. 101, pp. 25-33.
Nykanen et al., Cell, Nov. 2, 2001, vol. 107, pp. 309-321.
Elbashir et al., Genes & Dev. 2001, vol. 15, pp. 188-200.
Lipardi et al., Cell, Nov. 2, 2001, vol. 107 pp. 297-307.
Caplen et al., PNAS, Aug. 14, 2001, vol. 98, No. 17, pp. 9742-9747.
Drexler et al., Leukemia, 1996, vol. 10, pp. 588-599.
Nakao et al., Leukemia, 1996, vol. 10, pp. 1911-1918.
Yokota et al., Leukemia, 1997, vol. 11, pp. 1605-1609.
Kiyoi et al., Leukemia, 1997, vol. 11, pp. 1447-1452.
Gilliland et al., Blood, Sep. 1, 2002, vol. 100, No. 5, p. 1532-1542.
Levis et al., Blood, Jun. 1, 2002, vol. 99, No. 11, pp. 3885-3891.
O'Farrell et al., Blood, May 1, 2003, vol. 101, No. 9, pp. 3597-3605.
Giles et al., Blood, Aug. 1, 2003, vol. 102, No. 3, pp. 795-801.
Levis et al., Blood, Aug. 1, 2001, vol. 98, No. 3, pp. 885-887.

* cited by examiner

*Primary Examiner* — Sean McGarry
(74) *Attorney, Agent, or Firm* — Birch, Stewart, Kolasch & Birch, LLP

(57) ABSTRACT

To provide a means of controlling the function of Flt3. A composition for inhibiting the function of human Flt3, a method of inducing apoptosis by using the composition, and a kit for the method.

8 Claims, 2 Drawing Sheets

[FIG.1]
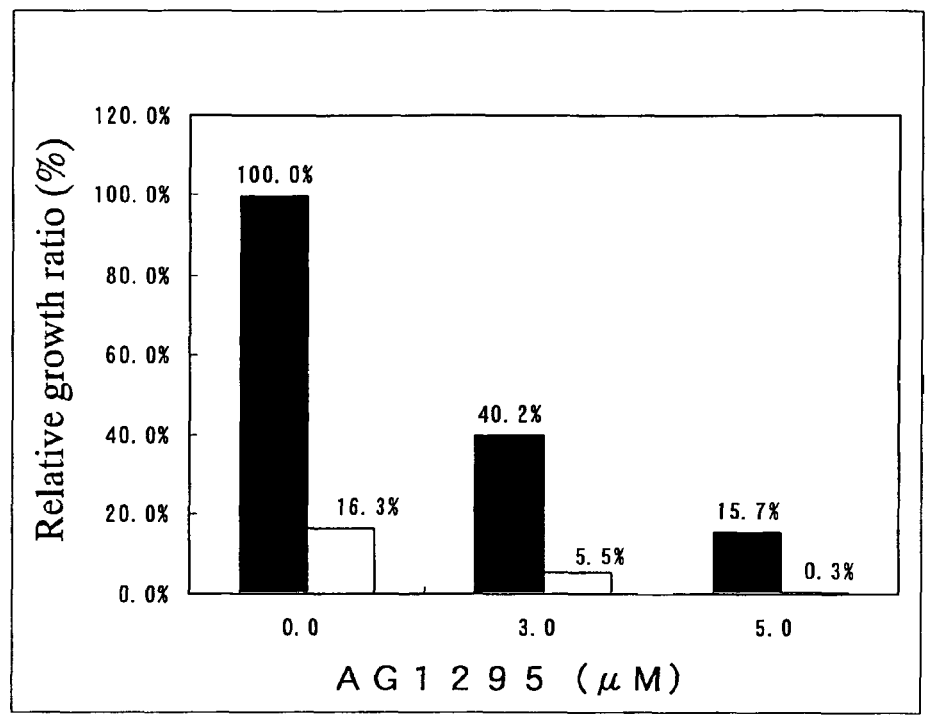
[FIG.2]
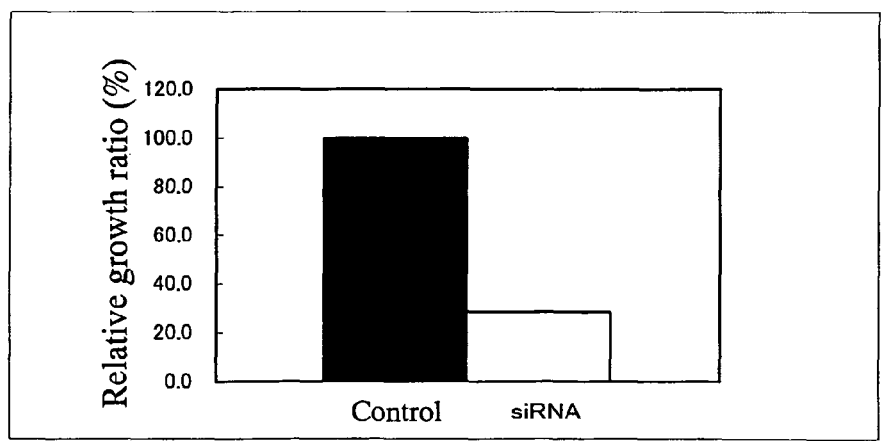

[FIG.3]
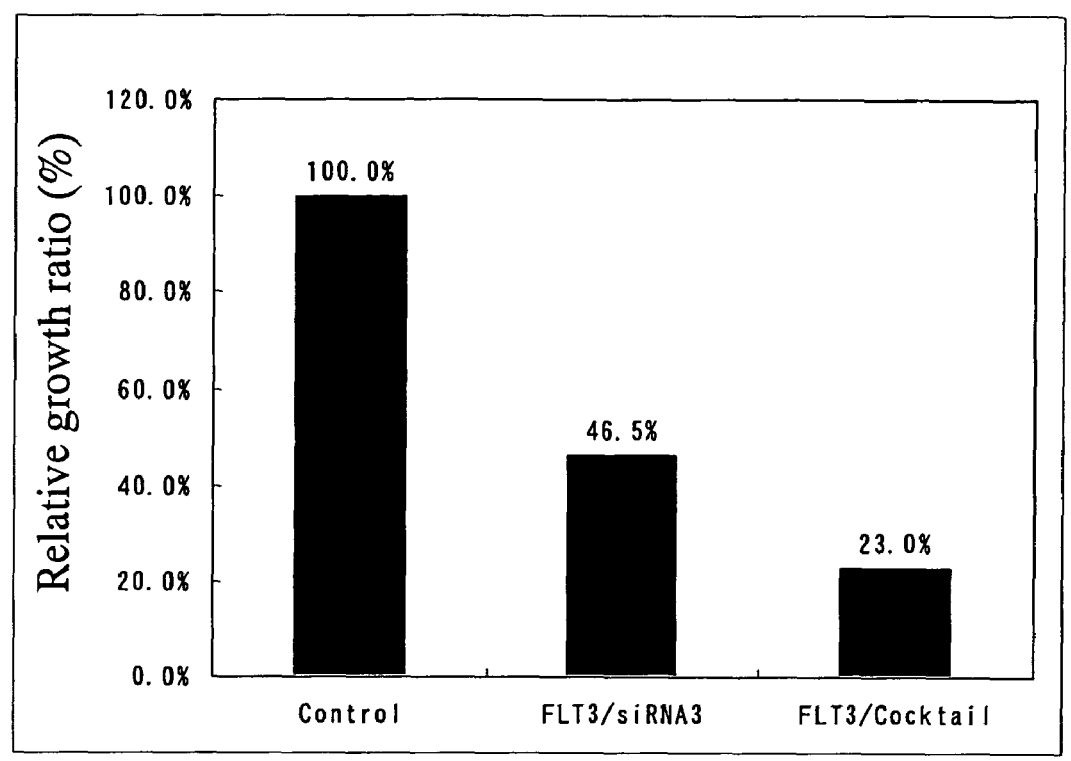

COMPOSITION FOR INHIBITING FUNCTION OF HUMAN FLT3

TECHNICAL FIELD

The present invention relates to a composition for inhibiting the function of human Flt3, a method of inducing apoptosis by using the composition, and a kit for the method.

BACKGROUND ART

Gene therapy of leukemia has been studied for many years (see, for example, Holt J. T. and two others, *Molecular Cellular Biology*, 8(2), pp. 963-973 (1988) or Bettinger T., Read M. L., *Current Opinion in Molecular Therapeutics*, 3(8), pp. 116-124 (2001)). Clinical study has also been actually initiated (see, for example, Verzeletti S. and six others, *Human Gene Therapy*, 9(15), pp. 2243-2251 (1998) or Wierda W. G., Kipps T. J., *Seminars in Oncology*, 27(5), pp. 502-511 (2000)). Further, RNA-based therapeutic techniques using antisense techniques and ribozyme techniques also have been under development (see, for example, Gewirtz A. M. and two others, *Blood*, 92(3), pp. 712-736 (1998)).

On the one hand, RNA interference (RNAi) in *Caenorhabditis elegans* reported in 1998 has attracted attention as a phenomenon of inhibiting gene expression by occurrence of sequence-specific mRNA degradation with double-stranded RNA (see, for example, Fire A. and five others, *Nature*, 391, pp. 806-811 (1998)). The above-mentioned RNA interference is considered to occur by a mechanism wherein long double-stranded RNA is cleaved into short RNA of 21 to 25 nucleotides called siRNA (short interfering RNA) by RNase III type activity called Dicer, and then the siRNA forms a ribonucleic acid/protein complex called RISC (RNA-induced silencing complex) and binds, in an ATP-dependent manner, to a target RNA, thereby degrading the target RNA (see, for example, Bernstein E. and three others, *Nature*, 409(6818), pp. 363-366 (2001), Tuschit and four others, *Genes and Development*, 13(24), pp. 3191-3197 (1999), Zamore P. D. and three others, *Cell*, 101(1), pp. 25-33 (2000), Nykanen A. and two others, *Cell*, 107(3), pp. 309-321 (2001), Elbashir S. M. and two others, *Genes and Development*, 15(2), pp. 188-200 (2001), and Lipardi C. and two others, *Cell*, 107(3), pp. 297-307 (2001)). Thereafter, it has been reported that the RNA interference can also be applied to mammalian cells to inhibit gene expression (see, for example, Elbashir S. M. and five others, *Nature*, 411(6836), pp. 494-498 (2001) or Caplen N. J. and four others, *Proc Natl Acad Sci USA*, 98(17), pp. 9742-9747 (2001)), and RNA interfering agents inhibiting expression of a chimera mRNA unique to leukemia, such as BCR-ABL and AML1-MTG8 have been reported (see, for example, Wilda M. and three others, *Oncogene*, 21(37), pp. 5716-5724 (2002) or Heidenreich O. and seven others, *Blood*, 101(8), pp. 3157-3163 (2003)).

On the one hand, it is reported that, in leukemic cells, high expression of Flt3 which is 1000 to 10000 times higher than that in normal myeloid cells is observed in 70 to 100% of AML (acute myeloid leukemia), ALL (acute lymphocytic leukemia), CML (chronic myeloid leukemia) and the like (see, for example, Drexler H. G., *Leukemia*, 10(4), pp. 588-599 (1996)). Further, tandem duplication mutation (Flt3/ITD mutation, ITD: internal tandem duplication) is found in a juxtamembrane region encoding a region just below a transmembrane region of Flt3, is detected in 20 to 30% of AML, 20% of APL (acute promyelocytic leukemia, which is referred to as AML:M3 in the present FAB classification) and 5% of MDS (myelodysplastic syndrome), and is suggested to be possibly an independent factor of pathosis or poor prognosis (see, for example, International Publication No. 00/11470 pamphlet, or Nakao M. and eight others, *Leukemia*, 10(21), pp. 1911-1918 (1996), Yokota S. and ten others, *Leukemia*, 11(10), pp. 1605-1609 (1997), Kiyoi H. and nineteen others, *Leukemia*, 11(9), pp. 1447-1452 (1997) and Gilliland D. G., Griffin J. D., *Blood*, 100(5), pp. 1532-1542 (2002)). Where the Flt3/ITD mutation occurs, there occurs ligand-independent kinase activation. As low-molecular-weight compounds inhibiting such Flt3 kinase activity, for example, CEP-701 (see, for example, Levis M. and nine others, *Blood*, 99(11), pp. 3885-3891 (2002)), SU11248 (see, for example, O'Farrell A. M. and fourteen others, *Blood*, 101(9), pp. 3597-3605 (2003)), SU5416 (see, for example, Giles F. J. and sixteen others, *Blood*, 102(3), pp. 795-801 (2003)), AG1295 (see, for example, Levis M. and four others, *Blood*, 98(3), pp. 885-887 (2001)) and the like have been studied, but no compound effective as a pharmaceutical preparation has been obtained at present.

DISCLOSURE OF INVENTION

One aspect of the present invention is to provide a composition which can achieve at least one of the followings: inhibition of the function of Flt3; inhibition of growth of Flt3 highly expressing cells and/or Flt3/ITD mutation-containing cells, for example, Flt3 highly expressing cancerous cells and/or Flt3/ITD mutation-containing cancerous cells; specifically, for example, Flt3 highly expressing leukemic cells and/or Flt3/ITD mutation-containing leukemic cells; preferential inhibition of growth of the above-mentioned cells; inhibition of the expression level of Flt3 gene; inhibition of a phenomenon based on mutation of a nucleic acid encoding Flt3; inhibition of Flt3-derived growth signal; inhibition of the expression level of Flt3 protein; and the like.

Other aspect of the present invention is to provide a composition which can achieve at least one of the followings: exhibition of the effect of the above-mentioned composition; expression of a nucleic acid which can inhibit the function of Flt3 in the above-mentioned composition in Flt3 highly expressing cells and/or Flt3/ITD mutation-containing cells, for example, Flt3 highly expressing cancerous cells and/or Flt3/ITD mutation-containing cancerous cells, specifically, for example, Flt3 highly expressing leukemic cells and/or Flt3/ITD mutation-containing leukemic cells; inhibition of the expression level of Flt3 gene in the cells; inhibition of a phenomenon based on mutation of a nucleic acid encoding Flt3 in the above-mentioned cells; inhibition of Flt3-derived growth signal in the cells; inhibition of the expression level of Flt3 protein in the cells; and the like.

A still other aspect of the present invention is to provide a method of inducing apoptosis, which can achieve at least one of the followings: inhibition of growth of Flt3 highly expressing cells and/or Flt3/ITD mutation-containing cells, for example, Flt3 highly expressing cancerous cells and/or Flt3/ITD mutation-containing cancerous cells, specifically, for example, Flt3 highly expressing leukemic cells and/or Flt3/ITD mutation-containing leukemic cells; preferential inhibition of growth of the above-mentioned cells; induction of apoptosis of the above-mentioned cells; inhibition of Flt3 derived growth signal in the above-mentioned cells; inhibition of the expression level of Flt3 protein in the above-mentioned cells; inhibition of the expression level of Flt3 gene in the above-mentioned cells; and the like.

Furthermore, another aspect of the present invention is to provide a composition and a kit for the above-mentioned method, which can achieve at least one of the followings:

efficient performance of the above-mentioned method of inducing apoptosis; inhibition of growth of Flt3 highly expressing cells and/or Flt3/ITD mutation-containing cells, for example, Flt3 highly expressing leukemic cells and/or Flt3/ITD mutation-containing leukemic cells; preferential inhibition of growth of the above-mentioned cells; induction of apoptosis of the above-mentioned cells; inhibition of Flt3-derived growth signal in the above-mentioned cells; inhibition of the expression level of Flt3 protein in the above-mentioned cells; inhibition of the expression level of Flt3 gene in the above-mentioned cells; and the like. The other concept, an object etc. of the present invention is also evident from the description of the present specification.

Specifically a first aspect of the present invention relates to a composition comprising a nucleic acid of which target is at least one region selected from the group consisting of a juxtamembrane region, a kinase region and an ATP-binding site region in human Flt3 and which can inhibit the function of Flt3.

In a second aspect, the present invention relates to a composition comprising a nucleic acid of which target is at least one region selected from the group consisting of the following (a) to (c) and which can inhibit the function of Flt3:
(a) a region corresponding to a cDNA nucleotide sequence of a juxtamembrane region in human normal Flt3 set forth in SEQ ID NO: 27,
(b) a region corresponding to a cDNA nucleotide sequence of a kinase region in human normal Flt3 set forth in SEQ ID NO: 28, and
(c) a region corresponding to a cDNA nucleotide sequence of an ATP-binding site region in human normal Flt3 set forth in SEQ ID NO: 29. The nucleic acid in the composition of the present invention is preferably a nucleic acid having a length of 15 to 25 bases. The nucleic acid includes, but is not particularly limited to, for example, a nucleic acid containing an RNA sequence corresponding to at least one nucleotide sequence selected from the group consisting of SEQ ID NOs: 1, 4, 7, 32, 35 and 38. Furthermore, the composition of the present invention includes, for example, those comprising a combination of a nucleic acid having a nucleotide sequence of SEQ ID NO: 2 and a nucleic acid having a nucleotide sequence of SEQ ID NO: 3, a combination of a nucleic acid having a nucleotide sequence of SEQ ID NO: 5 and a nucleic acid having a nucleotide sequence of SEQ ID NO: 6, a combination of a nucleic acid having a nucleotide sequence of SEQ ID NO: 8 and a nucleic acid having a nucleotide sequence of SEQ ID NO: 9, a combination of a nucleic acid having a nucleotide sequence of SEQ ID NO: 33 and a nucleic acid having a nucleotide sequence of SEQ ID NO: 34, a combination of a nucleic acid having a nucleotide sequence of SEQ ID NO: 36 and a nucleic acid having a nucleotide sequence of SEQ ID NO: 37, and a combination of a nucleic acid having a nucleotide sequence of SEQ ID NO: 39 and a nucleic acid having a nucleotide sequence of SEQ ID NO: 40, and the like.

In a third aspect, the present invention relates to a composition comprising a vector carrying a nucleic acid of which target is at least one region selected from the group consisting of a juxtamembrane region, a kinase region and an ATP-binding site region in human Flt3 and which can inhibit the function of Flt3.

In a fourth aspect, the present invention relates to a composition comprising a vector carrying a nucleic acid of which target is selected from the group consisting of the following (a) to (c) and which can inhibit the function of Flt3 in mammalian cells:

(a) a region corresponding to a cDNA nucleotide sequence of a juxtamembrane region in human normal Flt3 set forth in SEQ ID NO: 27,
(b) a region corresponding to a cDNA nucleotide sequence of a kinase region in human normal Flt3 set forth in SEQ ID NO: 28, and
(c) a region corresponding to a cDNA nucleotide sequence of an ATP-binding site region in human normal Flt3 set forth in SEQ ID NO: 29. The vector in the composition of the present invention may comprise a promoter such as an RNA polymerase III promoter or an RNA polymerase II promoter, as a promoter. The vector is not particularly limited, but it is desirable that the above-mentioned promoter is also a U6 promoter, an H1 promoter, a tRNA promoter, a CMV promoter, or the like. Furthermore, a vector selected from an adenovirus vector, a lentivirus vector and a retrovirus vector can be suitably used as a basic structure.

In a fifth aspect, the present invention relates to a method of inducing apoptosis, characterized by selectively inhibiting growth of Flt3 highly expressing cells and/or Flt3/ITD mutation-containing cells with the composition of the present invention, thereby inducing apoptosis of the Flt3 highly expressing cells and/or Flt3/ITD mutation-containing cells. In the method of inducing apoptosis according to the present invention, an agent inhibiting kinase may be used in addition to the composition of the present invention simultaneously or in a manner using one after another, to selectively inhibit growth of Flt3 highly expressing cells and/or Flt3/ITD mutation-containing cells, thereby inducing apoptosis of the Flt3 highly expressing cells and/or Flt3/ITD mutation-containing cells.

In the first to fifth aspects of the present invention, the composition of the present invention is also a composition for the above-mentioned efficient induction of apoptosis, inhibition of growth of Flt3 highly expressing cells and/or Flt3/ITD mutation-containing cells, for example, Flt3 highly expressing leukemic cells and/or Flt3/ITD mutation-containing leukemic cells, preferential inhibition of growth of the above-mentioned cells, induction of apoptosis of the above-mentioned cells, inhibition of Flt3-derived growth signal in the above-mentioned cells, inhibition of the expression level of Flt3 protein in the above-mentioned cells, inhibition of the expression level of Flt3 gene in the above-mentioned cells, or the like.

In a sixth aspect, the present invention relates to a kit containing the composition of the present invention. The kit can be also used as a kit for the above-mentioned efficient induction of apoptosis, inhibition of growth of Flt3 highly expressing cells and/or Flt3/ITD mutation-containing cells, for example, Flt3 highly expressing leukemic cells and/or Flt3/ITD mutation-containing leukemic cells, preferential inhibition of growth of the above-mentioned cells, induction of apoptosis of the above-mentioned cells, inhibition of Flt3-derived growth signal in the above-mentioned cells, inhibition of the expression level of Flt3 protein in the above-mentioned cells, inhibition of the expression level of Flt3 gene in the above-mentioned cells, or the like.

Specifically, the gist of the present invention relates to:
[1] a composition comprising a nucleic acid of which target is at least one region selected from the group consisting of a juxtamembrane region, a kinase region and an ATP-binding site region in human Flt3 and which can inhibit the function of Flt3,
[2] a composition comprising a nucleic acid of which target is at least one region selected from the group consisting of the following (a) to (c) and which can inhibit the function of Flt3:

(a) a region corresponding to a cDNA nucleotide sequence of a juxtamembrane region in human normal Flt3 set forth in SEQ ID NO: 27,
(b) a region corresponding to a cDNA nucleotide sequence of a kinase region in human normal Flt3 set forth in SEQ ID NO: 28, and
(c) a region corresponding to a cDNA nucleotide sequence of an ATP-binding site region in human normal Flt3 set forth in SEQ ID NO: 29,
[3] the composition according to the above-mentioned [1] or [2], wherein the composition comprises a nucleic acid having a length of 15 to 25 bases,
[4] the composition according to the above-mentioned [1] or [2], wherein the composition comprises an RNA sequence corresponding to at least one nucleotide sequence selected from the group consisting of SEQ ID NOs: 1, 4, 7, 32, 35 and 38,
[5] the composition according to any one of the above-mentioned [1] to [4], wherein the composition comprises a nucleic acid selected from the group consisting of:
a nucleic acid wherein a nucleic acid having a nucleotide sequence of SEQ ID NO: 2 and a nucleic acid having a nucleotide sequence of SEQ ID NO: 3 are combined,
a nucleic acid wherein a nucleic acid having a nucleotide sequence of SEQ ID NO: 5 and a nucleic acid having a nucleotide sequence of SEQ ID NO: 6 are combined,
a nucleic acid wherein a nucleic acid having a nucleotide sequence of SEQ ID NO: 8 and a nucleic acid having a nucleotide sequence of SEQ ID NO: 9 are combined,
a nucleic acid wherein a nucleic acid having a nucleotide sequence of SEQ ID NO: 33 and a nucleic acid having a nucleotide sequence of SEQ ID NO: 34 are combined,
a nucleic acid wherein a nucleic acid having a nucleotide sequence of SEQ ID NO: 36 and a nucleic acid having a nucleotide sequence of SEQ ID NO: 37 are combined, and
a nucleic acid wherein a nucleic acid having a nucleotide sequence of SEQ ID NO: 39 and a nucleic acid having a nucleotide sequence of SEQ ID NO: 40 are combined,
[6] a composition comprising a vector carrying a nucleic acid of which target is at least one region selected from the group consisting of a juxtamembrane region, a kinase region and an ATP-binding site region in human Flt3 and which can inhibit the function of Flt3,
[7] a composition comprising a vector carrying a nucleic acid of which target is a region selected from the group consisting of the following (a) to (c) and which can inhibit the function of Flt3 in mammalian cells:
(a) a region corresponding to a cDNA nucleotide sequence of a juxtamembrane region in human normal Flt3 set forth in SEQ ID NO: 27,
(b) a region corresponding to a cDNA nucleotide sequence of a kinase region in human normal Flt3 set forth in SEQ ID NO: 28, and
(c) a region corresponding to a cDNA nucleotide sequence of an ATP-binding site region in human normal Flt3 set forth in SEQ ID NO: 29,
[8] the composition according to the above-mentioned [6] or [7], wherein the nucleic acid has a nucleotide sequence of 15 to 25 bases of the target region,
[9] the composition according to the above-mentioned [6] or [7], wherein the composition comprises a vector carrying a nucleic acid corresponding to at least one nucleotide sequence selected from the group consisting of SEQ ID NOs: 1, 4, 7, 32, 35 and 38, and capable of expressing RNA corresponding to the nucleotide sequence,

[10] the composition according to any one of the above-mentioned [6] to [7], wherein the composition comprises a vector carrying a nucleic acid selected from the group consisting of:
a nucleic acid wherein a nucleic acid having a nucleotide sequence of SEQ ID NO: 2 and a nucleic acid having a nucleotide sequence of SEQ ID NO: 3 are combined,
a nucleic acid wherein a nucleic acid having a nucleotide sequence of SEQ ID NO: 5 and a nucleic acid having a nucleotide sequence of SEQ ID NO: 6 are combined,
a nucleic acid wherein a nucleic acid having a nucleotide sequence of SEQ ID NO: 8 and a nucleic acid having a nucleotide sequence of SEQ ID NO: 9 are combined,
a nucleic acid wherein a nucleic acid having a nucleotide sequence of SEQ ID NO: 33 and a nucleic acid having a nucleotide sequence of SEQ ID NO: 34 are combined,
a nucleic acid wherein a nucleic acid having a nucleotide sequence of SEQ ID NO: 36 and a nucleic acid having a nucleotide sequence of SEQ ID NO: 37 are combined, and
a nucleic acid wherein a nucleic acid having a nucleotide sequence of SEQ ID NO: 39 and a nucleic acid having a nucleotide sequence of SEQ ID NO: 40 are combined,
[11] the composition according to any one of the above-mentioned [6] to [10], wherein the composition comprises a vector having, as a promoter, an RNA polymerase III promoter or an RNA polymerase II promoter,
[12] the composition according to the above-mentioned [11], wherein the promoter is a promoter selected from the group consisting of a U6 promoter, an H1 promoter, a tRNA promoter and a CMV promoter,
[13] the composition according to any one of the above-mentioned [6] to [12], wherein the composition comprises, as a basic structure, a vector selected from an adenovirus vector, a lentivirus vector and a retrovirus vector,
[14] a method of inducing apoptosis, characterized by selectively inhibiting growth of FLT3 highly expressing cells and/or FLT3/ITD mutation-containing cells with the composition as defined in any one of the above-mentioned [1] to [13], thereby inducing apoptosis of the FLT3 highly expressing cells and/or FLT3/ITD mutation-containing cells,
[15] the method according to the above-mentioned [14], characterized by using an agent inhibiting kinase in addition to the composition simultaneously or in a manner using one after another, to selectively inhibit growth of FLT3 highly expressing cells and/or FLT3/ITD mutation-containing cells, thereby inducing apoptosis of the FLT3 highly expressing cells and/or FLT3/ITD mutation-containing cells, and
[16] a kit for carrying out the method as defined in the above-mentioned [14] or [15], wherein the kit comprises the composition as defined in any one of the above-mention [1] to [13].

The present invention provides a composition usable in inhibiting the function of Flt3, which is different from the conventional antisense techniques or ribozyme techniques. The present invention provides a composition containing a chemically synthesized nucleic acid (for example, siRNA) and its derivative or a composition containing a vector constructed so as to express the nucleic acid in a cell. The present invention also provides a method of inhibiting the function of Flt3 selectively or preferentially in Flt3 highly expressing cells and/or cells having Flt3/ITD mutation by utilizing the composition of the present invention, for example, a method of inducing apoptosis, as well as a kit for the method. The composition of the present invention exhibits an excellent effect such as the ability to: down-regulate the function of Flt3, preferentially inhibit growth of Flt3 highly expressing cells and/or Flt3/ITD mutation-containing cells, for example, Flt3 highly expressing cancerous cells and/or Flt3/ITD mutation-containing cancerous cells, specifically, for example, Flt3 highly expressing leukemic cells and/or Flt3/ITD mutation-containing leukemic cells, and induce apoptosis of the above-mentioned cells; inhibit Flt3-derived growth signal in the above-mentioned cells; inhibit the expression level of Flt3 protein in the above-mentioned cells; inhibit the expression level of Flt3 gene in the above-mentioned cells; or inhibit a phenomenon based on mutation of a nucleic acid encoding Flt3. The composition of the present invention exhibits an excellent effect such as the ability to: exhibit an effect of inhibiting the function of Flt3; express a nucleic acid which can inhibit the function of Flt3 in the above-mentioned cells; generate, e.g. RNA interference in the cells, to inhibit the expression level of Flt3 gene in the above-mentioned cells; inhibit a phenomenon based on mutation of a nucleic acid encoding Flt3; or inhibit the expression level of Flt3 protein. The method of inducing apoptosis according to the present invention exhibits an excellent effect such as the ability to preferentially inhibit growth of the above-mentioned cells and induce apoptosis of the above-mentioned cells. The kit of the present invention exhibits an excellent effect such as the ability to: efficiently perform the above-mentioned method of inducing apoptosis; and preferentially inhibit growth of the above-mentioned cells and induce apoptosis of the above-mentioned cells.

BRIEF DESCRIPTION OF THE DRAWINGS

FIG. 1 is a graph showing change in cell growth activity by using an siRNA in combination with a kinase inhibitor.

FIG. 2 is a graph showing the inhibition of cell growth by an siRNA expression vector.

FIG. 3 is a graph showing change in cell growth activity by using an siRNA alone or an siRNA cocktail.

BEST MODE FOR CARRYING OUT THE INVENTION

The present invention is based on the inventors' surprising finding that by down-regulating the function of Flt3 (FMS-like tyrosine kinase 3), growth of Flt3 highly expressing cells and/or Flt3/ITD mutation-containing cells can be preferentially inhibited and apoptosis can be induced. Therapy of patients with high expression of Flt3 and mutation of ITD as primary factors of poor prognosis of leukemia relies on bone marrow transplantation, and about 25% of patients with leukemia, that is, several tens of thousands of patients with Flt3 abnormalities, cannot be saved every year in the whole world at present. Therefore, it is expected that according to the present invention, the growth of leukemic cells is inhibited by inhibiting source of transduction of growth signals of leukemic cells by inhibiting high expression of Flt3 gene and/or expression of Flt3/ITD mutant gene or by regulating expression of Flt3 protein.

The above-mentioned Flt3 is a receptor of FL (Flt3 ligand), which is a growth factor of hematopoietic cells, and is one of membrane-associated tyrosine kinase receptors belonging to type III receptor tyrosine kinase (TRK) family including KIT (stem cell factor receptor), M-CSF (macrophage colony-stimulating factor) and PDGF (platelet-derived growth factor). The above-mentioned Flt3 is composed of five extracellular immunoglobulin-like domains, one transmembrane domain, a juxtamembrane domain following the transmembrane domain, and an intracellular kinase domain consisting of two subdomains TK1 and TK2. Receptor dimerization and activation of receptor kinase occur upon binding of FL to the above-mentioned Flt3, and signal transduction into cells is initiated.

The above-mentioned Flt3 is considered as an important molecule involved particularly in tumorigenesis and growth of hematopoietic cells. A mouse having a knockout Flt3 gene grows into a healthy mouse, but shows deficiency in initial hematopoietic cells, and in normal myeloid cells, those exhibiting the Flt3 gene are limited to CD34+ cells strongly exhibiting CD117.

(1) The Composition of the Present Invention

One aspect of the present invention relates to a composition comprising a nucleic acid of which target is at least one region selected from the group consisting of a juxtamembrane region, a kinase region and an ATP-binding site region in human Flt3 and which can inhibit the function of Flt3.

Another aspect of the present invention relates to a composition comprising a nucleic acid of which target is at least one region selected from the group consisting of the following (a) to (c) and which can inhibit the function of Flt3:

(a) a region corresponding to a cDNA nucleotide sequence of a juxtamembrane region in human normal Flt3 set forth in SEQ ID NO: 27, (b) a region corresponding to a cDNA nucleotide sequence of a kinase region in human normal Flt3 set forth in SEQ ID NO: 28, and (c) a region corresponding to a cDNA nucleotide sequence of an ATP-binding site region in human normal Flt3 set forth in SEQ ID NO: 29.

In this specification, the "juxtamembrane region in human Flt3" refers, for example, to a region of exons 13 to 14 in the Flt3 gene in healthy humans. This region is preferable as a target region of the nucleic acid contained in the composition of the present invention (that is, the nucleic acid which can inhibit the function of Flt3). The "juxtamembrane region in human Flt3" encompasses the "region corresponding to a cDNA nucleotide sequence of a juxtamembrane region in human normal Flt3". The above-mentioned "region corresponding to a cDNA nucleotide sequence of a juxtamembrane region in human normal Flt3" refers to a region corresponding to a region of a cDNA nucleotide sequence of a juxtamembrane region in human normal Flt3 set forth in a nucleotide sequence of SEQ ID NO: 27, which also includes, but is not particularly limited to, for example, regions of sequences wherein in the above-mentioned SEQ ID NO: 27, a nucleotide is added, substituted, deleted, inserted, or the like. In the exons 14 to 15 containing the above-mentioned juxtamembrane region, a region of the sequence having Flt3/ITD mutation is also included in the "target region of the nucleic acid which can inhibit the function of Flt3" contained in the composition of the present invention, that is, the "region corresponding to a cDNA nucleotide sequence of a juxtamembrane region in human normal Flt3". The amino acid sequence and cDNA sequence of human normal Flt3 are exemplified by sequences disclosed in, for example, Gene Bank Accession No: NM_004119, etc.

In this specification, the "kinase region in human Flt3" refers, for example, to a region of exon 15 to exon 19 in the Flt3 gene in healthy humans. The above-mentioned region is preferable as a target region of the nucleic acid contained in the composition of the present invention (that is, the nucleic acid which can inhibit the function of Flt3). The "kinase region in human Flt3" encompasses the "region corresponding to a cDNA nucleotide sequence of a kinase region in human normal Flt3". The above-mentioned "region corresponding to a cDNA nucleotide sequence of a kinase region in human normal Flt3" refers to a region corresponding to the region of a cDNA nucleotide sequence of a kinase region in human normal Flt3 set forth in SEQ ID NO: 28, which also includes, but is not particularly limited to, for example, regions of sequences wherein in SEQ ID NO: 28, a nucleotide is added, substituted, deleted, inserted or the like.

In this specification, the "ATP-binding site region in human Flt3" refers, for example, to a region of exon 14 to exon 19 of the Flt3 gene in healthy humans. This region is preferable as a target region of the nucleic acid contained in the composition of the present invention (that is, the nucleic acid which can inhibit the function of Flt3). The "ATP-binding site region in human Flt3" also encompasses the "region corresponding to a cDNA nucleotide sequence of an ATP-binding site region in human normal Flt3". The above-mentioned "region corresponding to a cDNA nucleotide sequence of an ATP-binding site region in human normal Flt3" refers to a region corresponding to the region of a cDNA nucleotide sequence of an ATP-binding region in human normal Flt3 set forth in a nucleotide sequence of SEQ ID NO: 29, which also includes, but is not particularly limited to, for example, regions of sequences wherein in SEQ ID NO: 29, a nucleotide is added, substituted, deleted, inserted, or the like.

One great feature of the composition of the present invention is that the composition comprises a nucleic acid for inhibiting the function of human Flt3, wherein the target region of the nucleic acid is at least one region selected from the group consisting of the above-mentioned juxtamembrane region, kinase region and ATP-binding site region in human Flt3 or at least one region selected from the group consisting of the above-mentioned (a) to (c). The above-mentioned target region may be one region or plural regions. Therefore, the composition of the present invention can be optionally constructed on the basis of the nucleotide sequences of the above regions, according to the Examples described later. According to the composition of the present invention, since the RNA interference agent is targeted to the above region, there is exhibited an excellent effect by which the function of Flt3 can be effectively down-regulated.

In this specification, the phrase "which can inhibit the function of Flt3" includes, but is not particularly limited to, the ability to inhibit the expression of Flt3 gene, the function and/or expression of Flt3-derived growth signal or the expression of Flt3 protein. In other words, such concept also encompasses the ability to, for example: inhibit transcription of Flt3 gene; unstabilize the mRNA after transcription; inhibit translation from the Flt3 mRNA; or inhibit the function of the amino acid sequence after translation. In another aspect, the phrase "which can inhibit the function of Flt3" may be inhibition of growth of Flt3 highly expressing cells and/or Flt3/ITD mutation-containing cells, for example, Flt3 highly expressing leukemic cells and/or Flt3/ITD mutation-containing leukemic cells, preferential inhibition of growth of the above-mentioned cells, induction of apoptosis of the above-mentioned cells, inhibition of Flt3-derived growth signal in the above-mentioned cells, inhibition of the expression level of Flt3 protein in the above-mentioned cells, or inhibition of the expression level of Flt3 gene in the above-mentioned cells. The above-mentioned nucleic acid "which can inhibit the function of Flt3" includes, but is not particularly limited to, for example, an siRNA.

Accordingly, the composition of the present invention exhibits an excellent effect such as the ability to preferentially inhibit the growth of Flt3 highly expressing cells and/or Flt3/ITD mutation-containing cells, for example, Flt3 highly expressing cancerous cells and/or Flt3/ITD mutation-containing cancerous cells, specifically, for example, Flt3 highly expressing leukemic cells and/or Flt3/ITD mutation-containing leukemic cells. In another aspect, since the composition of the present invention is targeted to at least one region selected from the group consisting of a juxtamembrane region, a kinase region and an ATP-binding site region in human Flt3 or at least one region of the above-mentioned (a) to (c), the composition can inhibit a phenomenon based on mutation of a nucleic acid encoding Flt3.

In this specification, the "Flt3 highly expressing cells" include any of cells highly expressing Flt3 mRNA, cells having increased Flt3-derived growth signals, cells highly expressing Flt3 protein, etc. The above-mentioned "Flt3 highly expressing cancerous cells" include any of cancerous cells highly expressing Flt3 mRNA, cancerous cells having increased Flt3-derived growth signals, cancerous cells highly expressing Flt3 protein, etc. The "Flt3 highly expressing leukemic cells" include any of leukemic cells highly expressing Flt3 mRNA, leukemic cells having increased Flt3-derived growth signals, leukemic cells highly expressing Flt3 protein, etc.

Furthermore, the "Flt3/ITD mutation-containing cells" include any of cells having tandem duplication mutation absent in healthy humans in a region of exons 14 to 15 in a juxtamembrane region of Flt3, that is, cells highly expressing mRNA derived from the mutation, cells having increased Flt3-derived growth signals caused by the mutation, cells highly expressing the mutant Flt3 protein, etc. The "Flt3/ITD mutation-containing cancerous cells" include any of cancerous cells having tandem duplication mutation absent in healthy humans in a region of exons 14 to 15 in a juxtamembrane region of Flt3, that is, cancerous cells highly expressing mRNA derived from the mutation, cancerous cells having increased Flt3-derived growth signals caused by the mutation, cancerous cells highly expressing the mutant Flt3 protein, etc. The "Flt3/ITD mutation-containing leukemic cells" include any of leukemic cells having tandem duplication mutation absent in healthy humans in a region of exons 14 to 15 in a juxtamembrane region of Flt3, that is, leukemic cells highly expressing mRNA derived from the mutation, leukemic cells having increased Flt3-derived growth signals caused by the mutation, leukemic cells highly expressing the mutant Flt3 protein, etc.

The above-mentioned "phenomenon based on mutation of a nucleic acid encoding Flt3" includes, for example, hematopoietic tumors, specifically leukemia, more specifically acute myeloid leukemia (AML), acute promyelocytic leukemia (APL), acute lymphocytic leukemia (ALL), myelodysplastic syndrome (MDS), and the like.

The "nucleic acid which can inhibit the function of Flt3" contained in the composition of the present invention includes, but is not particularly limited to, siRNA for RNA interference, and in the case of the siRNA, from the viewpoint of inhibition of interferon response in mammalian cells, the nucleic acid is exemplified by those having a length of, for example, 15 to 29 bases, preferably a length of 15 to 25 base pairs, more preferably a length of 20 to 25 base pairs. All of the above-mentioned nucleotide sequence of the length may be a nucleotide sequence of the target region, and a part thereof may be a nucleotide sequence of the target region. From the viewpoint of effectiveness of RNA interference in mammalian cells, the nucleic acid in the composition of the present invention may be, for example, preferably in the form of double-stranded RNA having 2 to 4 bases protruded at the 3'-end, more preferably in the form of double-stranded RNA having 2 bases protruded at the 3'-end. These 2 to 4 bases are exemplified by TT to TTTT sequences.

One embodiment of the present invention may be a composition containing a nucleic acid of which target is a region of the tandem duplication mutation of Flt3 gene not found in healthy humans. The "tandem duplication mutation" refers to a mutation wherein a nucleotide sequence of dozens of nucleotides undergoes tandem duplication in the juxtamembrane region of Flt3 gene. The above-mentioned tandem duplication mutation includes those having diversification with respect to the degree of tandem duplication, the sequence undergoing tandem duplication, and the like, depending on each individual (case).

In other words, when the tandem duplication mutation is a target, a nucleic acid corresponding to a nucleotide sequence containing the tandem duplication mutation region in each of the above-mentioned individual cases can be used. The nucleic acid is not particularly limited, and may be, for example, siRNA for RNA interference. By using the tandem duplication mutation region, only those cells having the tandem duplication mutation of Flt3 gene can be subjected to RNA interference, resulting in inhibition of the function of Flt3.

The composition of the present invention can selectively inhibit the growth of Flt3 highly expressing leukemic cells and/or Flt3/ITD mutation-containing leukemic cells, and induce apoptosis of the cells.

The method of designing the "nucleic acid which can inhibit the function of Flt3" contained in the composition of the present invention is described below in detail taking siRNA for RNA interference for example. In the case of the siRNA, the siRNA can be designed by (I) step of secondary structure prediction and (II) step of siRNA sequence selection.

The above-mentioned (I) secondary structure prediction can be carried out by predicting, with a program etc., a secondary structure of a gene to be inhibited. From the viewpoint of efficient generation of RNA interference, it is preferable that a site having a strong secondary structure is avoided. The above-mentioned secondary structure prediction program to be used can be, but is not particularly limited to, an MFOLD program (http://bioweb.pasteur.fr/seqanal/interfaces/mfold-simple.html).

In the above-mentioned (II) siRNA sequence selection, the sequence is not particularly limited and may be a sequence of the target region or a sequence of the region corresponding to a nucleotide sequence of the nucleic acid which can inhibit the function of Flt3, and any nucleotide sequences of a promoter region, a structural gene region, a 5'-untranslated region, a 3'-untranslated region and a region around an initiation codon can be preferably used. For example, when the sequence of the target region is selected, it is desirable that in a region downstream by 75 nucleotide residues or more from the initiation codon of the sequence in the nucleic acid encoding Flt3, more preferably in a region downstream by 1687 to 2347 nucleotide residues therefrom, two consecutive adenylic acid residues, or two adenylic acid residues and one guanylic acid residue, are used as a sense strand. When the siRNA sequence is prepared, it is desirable that the sequence is a sequence consisting of arbitrary 13 to 29 nucleotide residues after two consecutive adenylic acid residues, more preferably a sequence consisting of one guanylic acid residue and arbitrary 20 nucleotide residues or a sequence consisting of one cytidylic acid residue and arbitrary 20 nucleotide residues. The GC content of the sense strand is not particularly limited, but can be preferably 30 to 70%, more preferably 40 to 60%. For preventing unspecific action, it is desirable that homology search for nucleotide sequence is carried out in the stage of design, to confirm that the sequence is a sequence specific for the target sequence, that is, a sequence poor in sequence homology to known sequences in a database and specific for the target sequence.

The nucleic acid contained in the composition of the present invention is not particularly limited, but from the viewpoint of the sequence which can inhibit the function of Flt3 expressed in mammalian cells, the nucleic acid is preferably a nucleic acid containing an RNA sequence corresponding to at least one nucleotide sequence selected from the group consisting of, for example, SEQ ID NOs: 1, 4, 7, 32, 35 and 38. The composition of the present invention is exemplified by a composition containing at least one nucleic acid selected from the group consisting of: a combination of nucleotide sequences set forth in SEQ ID NOs: 2 and 3, SEQ ID NOs: 5 and 6, SEQ ID NOs: 8 and 9, SEQ ID NOs: 33 and 34, SEQ ID NOs: 36 and 37, or SEQ ID NOs: 39 and 40, that is, a nucleic acid wherein a nucleic acid having a nucleotide sequence of SEQ ID NO: 2 and a nucleic acid having a nucleotide sequence of SEQ ID NO: 3 are combined, a nucleic acid wherein a nucleic acid having a nucleotide sequence of SEQ ID NO: 5 and a nucleic acid having a nucleotide sequence of SEQ ID NO: 6 are combined, a nucleic acid wherein a nucleic acid having a nucleotide sequence of SEQ ID NO: 8 and a nucleic acid having a nucleotide sequence of SEQ ID NO: 9 are combined, a nucleic acid wherein a nucleic acid having a nucleotide sequence of SEQ ID NO: 33 and a nucleic acid having a nucleotide sequence of SEQ ID NO: 34 are combined, a nucleic acid wherein a nucleic acid having a nucleotide sequence of SEQ ID NO: 36 and a nucleic acid having a nucleotide sequence of SEQ ID NO: 37 are combined, and a nucleic acid wherein a nucleic acid having a nucleotide sequence of SEQ ID NO: 39 and a nucleic acid having a nucleotide sequence of SEQ ID NO: 40 are combined.

The nucleic acid contained in the composition of the present invention is preferably desirable to be composed of deoxyribonucleotides and/or ribonucleotides. The nucleic acid is not particularly limited, may be a nucleic acid having an inhibitory action on the function of Flt3, and may be a single- or double-stranded nucleic acid. The nucleic acid contained in the composition of the present invention is not particularly limited, and can be synthesized by a chemical synthesis method using a protective group such as 2'-ACE (2'-bis(acetoxymethoxy)-methylether) or 2'-TBDMS (2'-t-butyldimethylsilyl).

The nucleic acid synthesized by a chemical synthesis method is not particularly limited, but may be modified with a chemically-modifying group for stabilization or labeling. The modification usable in the present invention is not particularly limited, and includes, for example, addition of 6-fluorescein, addition of biotin, 2'-O-methylation, PNA (peptide nucleic acid), amino group, etc. The modifying group may be added to any of the 5'- or 3'-terminal or internal nucleotides as long as the RNA interference action is not inhibited.

Another aspect of the composition of the present invention relates to a composition comprising a vector carrying a nucleic acid of which target is at least one region selected from the group consisting of a juxtamembrane region, a kinase region and an ATP-binding site region in human Flt3 and which can inhibit the function of Flt3.

Another aspect of the present invention relates to a composition comprising a vector carrying the above-mentioned nucleic acid, for example, a nucleic acid of which target is a region selected from the group consisting of the following (a) to (c) and which can inhibit the function of Flt3 in a mammalian cell:

(a) a region corresponding to a cDNA nucleotide sequence of a juxtamembrane region in human normal Flt3 set forth in SEQ ID NO: 27,
(b) a region corresponding to a cDNA nucleotide sequence of a kinase region in human normal Flt3 set forth in SEQ ID NO: 28, and
(c) a region corresponding to a cDNA nucleotide sequence of an ATP-binding site region in human normal Flt3 set forth in SEQ ID NO: 29, Specifically, for example, a composition comprising a vector carrying a nucleic acid which corresponds to at least one nucleotide sequence selected from the group consisting of SEQ ID NOs: 1, 4, 7, 32, 35 and 38 and which can express an RNA corresponding to the nucleotide sequence, more specifically, for example, a composition comprising a vector carrying a nucleic acid selected from the group consisting of:
a nucleic acid wherein a nucleic acid having a nucleotide sequence of SEQ ID NO: 2 and a nucleic acid having a nucleotide sequence of SEQ ID NO: 3 are combined,
a nucleic acid wherein a nucleic acid having a nucleotide sequence of SEQ ID NO: 5 and a nucleic acid having a nucleotide sequence of SEQ ID NO: 6 are combined,
a nucleic acid wherein a nucleic acid having a nucleotide sequence of SEQ ID NO: 8 and a nucleic acid having a nucleotide sequence of SEQ ID NO: 9 are combined,
a nucleic acid wherein a nucleic acid having a nucleotide sequence of SEQ ID NO: 33 and a nucleic acid having a nucleotide sequence of SEQ ID NO: 34 are combined,
a nucleic acid wherein a nucleic acid having a nucleotide sequence of SEQ ID NO: 36 and a nucleic acid having a nucleotide sequence of SEQ ID NO: 37 are combined, and
a nucleic acid wherein a nucleic acid having a nucleotide sequence of SEQ ID NO: 39 and a nucleic acid having a nucleotide sequence of SEQ ID NO: 40 are combined.

The composition of the present invention comprises a vector which can maintain and express a nucleic acid of which target is at least one region selected from the group consisting of a juxtamembrane region, a kinase region and an ATP-binding site region in human Flt3 or at least one region selected from the group consisting of the above-mentioned (a) to (c) and which inhibit the function of Flt3, thus enabling exhibition of the effect of the above-mentioned nucleic acid, expression of the nucleic acid inhibiting the above-mentioned function of Flt3 in the above-mentioned cells and inhibition of the phenomenon based on mutation of the nucleic acid encoding Flt3 in the above-mentioned cells. The target region may be one region or plural regions.

The vector contained in the composition of the present invention is not particularly limited with respect to a basic vector as long as it is a vector which maintains and expresses the nucleic acid which can inhibit the function of Flt3 in mammalian cells and which can express the nucleic acid efficiently in the cells. The above-mentioned basic vector includes, but is not particularly limited to, for example, a plasmid vector and a virus vector such as adenovirus vector, adeno-associated virus vector, retrovirus vector and lentivirus vector. The above-mentioned plasmid vector includes, but is not particularly limited to, for example, plasmid vectors expressing nucleic acid for RNA interference, such as piGENE tRNA plasmid (trade name, manufactured by iGENE), siLentGene (trade name, manufactured by Promega) and pSEC Hygro Vector (trade name, manufactured by Ambion). The above-mentioned adenovirus vector includes BD Knockout Adenoviral RNAi System (trade name, manufactured by Becton Dickinson). The retrovirus vector includes pSIREN-RetroQ Vector (trade name, manufactured by Becton Dickinson) or the like.

The promoter used in the vector contained in the composition of the present invention is not particularly limited as long as it is capable of functioning in mammalian cells, and the promoter includes, for example, an RNA polymerase II promoter, an RNA polymerase III promoter, and a promoter which can be regulated by tetracycline, and the like. It is also advantageous in that use of a tissue-specific promoter enables expression of the nucleic acid which can inhibit the function of Flt3 in a desired site, an organ etc. For example, the above-mentioned RNA polymerase II promoter includes, but is not particularly limited to, a CMV promoter, etc. The above-mentioned RNA polymerase III promoter includes a tRNA promoter, a U6sn RNA promoter, a histone H1 promoter etc. The above-mentioned promoter which can be regulated by tetracycline includes a tetracycline-regulated U6 promoter, TR promoter and the like. The above-mentioned promoter can be combined with Cre-loxP system to regulate the expression more strictly.

The vector can be constructed, for example, by constructing the above-mentioned nucleic acid which can inhibit the function of Flt3, in the step of (I) secondary structure prediction and the step of (II) siRNA sequence selection and then integrating the resulting nucleic acid into a suitable vector such that the nucleic acid can be maintained and expressed.

Construction of the above-mentioned vector is not particularly limited, and for example, the vector for RNA interference can be constructed as (A) a vector of tandem type for transcribing a sense RNA and an antisense RNA separately wherein a nucleic acid encoding a sense RNA for the above-mentioned nucleic acid and a nucleic acid encoding an antisense RNA are arranged in a forward direction under the control of two different promoters, (B) a vector for transcribing a stem loop-type (or hair pin-type) RNA comprising a sense RNA ligated via a loop with an antisense RNA, wherein a nucleic acid encoding a sense RNA for the RNA interfering agent of the present invention and a nucleic acid encoding an antisense RNA are arranged in a reverse direction under the control of one promoter, or (C) a vector of opposite type wherein a nucleic acid encoding an RNA is arranged under the control of a promoter functioning on the sense strand of the vector and a nucleic acid encoding an RNA complementary to the former RNA is arranged under the control of a promoter functioning on the antisense strand, thereby each RNA is transcribed under the control of the respective promoter. The RNA interference vector of the present invention is not particularly limited, but it is desirable that which one of the tandem-type, stem-loop type and opposite-type vectors is used is determined depending on the type of reaction conditions, for example, the type of mammalian cells and the type of the sense sequence and antisense sequence, or the like.

In the above-mentioned vector, the nucleotide sequence of the nucleic acid which can inhibit the function of Flt3 is not particularly limited as long as it is a sequence exhibiting a sequence-specific inhibitory action such as RNAi interference action, but when the RNA polymerase III promoter is used, it is desirable to satisfy the following two conditions:
the initiation site should be a purine residue [guanylic acid residue (G) or adenylic acid residue (A)], and
two bases before the initiation site should be AA because four consecutive uracil residues are added to the 3'-end of the antisense strand. In addition, when the RNA polymerase II promoter is used, it is desired that
the vector should be of stem-loop type, and
a short poly(A) sequence should be added.

Hereinafter, a method of preparing the vector carrying the nucleic acid which can inhibit the function of Flt3 is described in detail taking a vector for RNA interference for example.

Specifically, the siRNA sequence is selected, for example, for the juxtamembrane region, ATP-binding site region and kinase activity region in Flt3 as described above, and the vector is constructed so as to transcribe the siRNA. On the other hand, the expression vector used in transcription of the siRNA, that is, the composition of the present invention, can be obtained by preparing, by PCR, a sequence generating siRNA by transcription, inserting the resulting sequence downstream of a U6 RNA polymerase promoter (that is, U6 promoter) to prepare an expression cassette, and ligating the resulting expression cassette with a skeleton of a suitable vector, or by chemically synthesizing a DNA generating the siRNA by transcription, adding a tag of a recognition sequence of a restriction enzyme, and inserting the resulting product into a vector. Then, cells expressing the objective mRNA are transfected with a composition containing the resulting vector by an electroporation method or a lipofection method, or by cotransfection with the target gene, whereby inhibition of expression of the objective mRNA is screened. From the viewpoint of improving the efficiency of transfection to the cells, on the other hand, a vector having the expression cassette inserted into an adenovirus, retrovirus or lentivirus vector can be utilized as the composition of the present invention.

Thus, the composition of the present invention is a composition containing a nucleic acid which can inhibit the function of Flt3 or a vector carrying the nucleic acid, and can be further prepared in combination with a pharmaceutically acceptable known carrier, and can be formulated depending on its intended use. For example, the composition can be formed into a pharmaceutical composition such as an injection or a solution for drop. Furthermore, the composition of the present invention also encompasses the composition containing a component for stabilization of the above-mentioned active ingredient or for introduction into cells. The dose of the composition as a pharmaceutical composition is determined suitably depending on the preparation form, the administration method, the intended use, and the age, weight and symptom of the patient into which it is administered.

(2) Method of Inducing Apoptosis of Flt3 Highly Expressing Cells by Using the Composition of the Present Invention Another aspect of the present invention relates to a method of inducing apoptosis, selectively inhibiting growth of Flt3 highly expressing leukemic cells and/or Flt3/ITD mutation-containing leukemic cells with the composition of the present invention, and inducing apoptosis.

Specifically, in one embodiment, the method of inducing apoptosis according to the present invention relates to a method of inducing apoptosis, characterized by selectively inhibiting growth of Flt3 highly expressing cells and/or Flt3/ITD mutation-containing cells with the composition of the present invention, and inducing the apoptosis of the Flt3 highly expressing cells and/or Flt3/ITD mutation-containing cells.

Since the method of inducing apoptosis according to the present invention uses the composition of the present invention, the method can preferentially inhibit growth of Flt3 highly expressing cells and/or Flt3/ITD mutation-containing cells, for example, Flt3 highly expressing cancerous cells and/or Flt3/ITD mutation-containing cancerous cells, specifically for example, Flt3 highly expressing leukemic cells and/or Flt3/ITD mutation-containing leukemic cells, thus inducing the apoptosis of the cells.

The method of inducing apoptosis according to the present invention may be combined with a method using an agent inhibiting kinase. The above-mentioned agent inhibiting kinase includes, preferably an agent inhibiting tyrosine kinase, more preferably an agent inhibiting Flt3 kinase. The above-mentioned agent inhibiting kinase includes, but is not particularly limited to, for example, indocarbazole derivative CEP-701 (manufactured by Cephalon, Inc), quinazoline-based compound CT53518 (manufactured by Millennium Pharmaceuticals), staurosporine derivative PKC412 (CGP41251, manufactured by Novartis), indolinone-based compound SU11248 (manufactured by Sugen, Inc.), methanone derivatives D-64406 and D-65476 (manufactured by ASTA Medica), AG1295 (manufactured by CALBIOCHEM) or the like.

Specifically, any of the above-mentioned agents inhibiting kinase can be suitably used as long as it can selectively inhibit expression of Flt3 kinase to induce apoptosis by its synergistic effect with the composition of the present invention.

Specifically, due to the method of inducing apoptosis according to the present invention, the composition of the present invention is introduced into Flt3 highly expressing cells and/or Flt3/ITD mutation-containing cells, for example, Flt3 highly expressing cancerous cells and/or Flt3/ITD mutation-containing cancerous cells, specifically, for example, Flt3 highly expressing leukemic cells and/or Flt3/ITD mutation-containing leukemic cells, thereby growth of the cells can be selectively inhibited, to induce the apoptosis of the cells.

A known method of introducing a gene can be used in introduction of the composition of the present invention into Flt3 highly expressing cells and/or Flt3/ITD mutation-containing cells, specifically Flt3 highly expressing cancerous cells and/or Flt3/ITD mutation-containing cancerous cells, more specifically Flt3 highly expressing leukemic cells and/or Flt3/ITD mutation-containing leukemic cells. The method includes, but is not particularly limited to, for example, an electroporation method, injection into tissues, a hydrodynamics method, microinjection, transfection, a lipofection method, a method of bombardment with gold particles, a calcium phosphate method, a DEAE dextran method, a method using micelle particles, a method using reversed micelle particles, a method using low-density lipoprotein, a method using transferrin, a method using atherocollagen, a method using a virus vector such as an adenovirus vector, a lentivirus vector or a retrovirus vector, a method using a membrane-permeable peptide, a method using a membrane fusion peptide, and the like.

When the above-mentioned agent inhibiting kinase is used, the agent can be used simultaneously or in a manner using one after another, to selectively inhibit growth of Flt3 highly expressing cells and/or Flt3/ITD mutation-containing cells, thereby inducing the apoptosis of the Flt3 highly expressing cells and/or Flt3/ITD mutation-containing cells.

Inhibition of growth of Flt3 highly expressing cells and/or Flt3/ITD mutation-containing cells can be evaluated by a gene amplification method, a nucleic acid hybridization method, a method using an antibody, etc. which are known. The method can be performed by, but is not particularly limited to, for example, an RT-PCR method, a real-time RT-PCR method, a Northern blotting method, as Western blotting method, enzyme immunoassay (EIA), ELISA, an immunostaining method, and the like.

The apoptosis of Flt3 highly expressing cells and/or Flt3/ITD mutation-containing cells can be evaluated using a known method. The method can be performed by, but is not particularly limited to, for example, observation of morphological change of the cells, detection of DNA fragmentation in the cells, detection of extracellular leakage of lactate dehydrogenase etc., a TUNEL method, an MTT method, ELISA, an immunostaining method, etc.

Since the method of inducing apoptosis according to the present invention can selectively inhibit the growth of Flt3 highly expressing leukemic cells and/or Flt3/ITD mutation-containing leukemic cells of a patient with leukemia having the cells, and induce the apoptosis of the cells, the method can also be utilized as a method of treating the leukemia in which the above-mentioned Flt3 gene is involved.

The therapeutic effect on leukemia can be examined by a known method. For example, the therapeutic effect can be evaluated by procedures which include, but are not particularly limited to, confirmation of an image of leukocytes in bone marrow and peripheral blood, confirmation of leukocytes by an RT-PCR method, confirmation by immunostaining, confirmation by ELISA, etc.

(3) Kit for Carrying out the Method of Inducing Apoptosis

In another aspect, the present invention relates to a kit for carrying out the above-mentioned method of inducing apoptosis.

Since the kit of the present invention comprises the composition of the present invention, the method of inducing apoptosis can be efficiently carried out, to achieve preferential inhibition of growth of the Flt3 highly expressing cells and/or Flt3/ITD mutation-containing cells, for example, Flt3 highly expressing cancerous cells and/or Flt3/ITD mutation-containing cancerous cells, specifically, for example, Flt3 highly expressing leukemic cells and/or Flt3/ITD mutation-containing leukemic cells, thus inducing the apoptosis of the cells.

The kit of the present invention may further comprise a buffer solution stabilizing the composition of the present invention. The kit of the present invention may further comprise a reagent used in a known gene introduction method for introducing the composition of the present invention, which includes, but is not particularly limited to, for example, an electroporation method, injection into tissues, a hydrodynamics method, a lipofectamine method, microinjection, a calcium phosphate method, a DEAE dextran method, and the like.

The kit of the present invention may further comprise a DNA-dependent RNA polymerase for transcribing the nucleic acid which can inhibit the function of Flt3 from the vector carrying the nucleic acid.

The composition or kit of the present invention can be used to selectively inhibit growth of Flt3 highly expressing leukemic cells and/or Flt3/ITD mutation-containing leukemic cells, and induce the apoptosis of the cells.

A known method of introducing a gene can be used to introduce the composition of the present invention into Flt3 highly expressing cells and/or Flt3/ITD mutation-containing cells, specifically Flt3 highly expressing cancerous cells and/or Flt3/ITD mutation-containing cancerous cells, more specifically Flt3 highly expressing leukemic cells and/or Flt3/ITD mutation-containing leukemic cells. The method can be performed by, but is not particularly limited to, for example, an electroporation method, injection into tissues, a hydrodynamics method, microinjection, transfection, a lipofection method, a method of bombardment with gold particles, a calcium phosphate method, a DEAE dextran method, a method using micelle particles, a method using reversed micelle particles, a method using low-density lipoprotein, a method using transferrin, a method using atherocollagen, a method using a virus vector such as an adenovirus vector, a lentivirus vector or a retrovirus vector, a method using a membrane-permeable peptide, a method using a membrane fusion peptide, and the like.

The present invention is described in more detail by means of the following Examples, but the present invention is not particularly limited to the scope of the Examples.

EXAMPLE 1

(1) Synthesis and Selection of a Nucleic Acid which can Inhibit Function of Flt3

The effectiveness of a composition containing a nucleic acid of which target is an ATP-binding site region, a kinase region (TK region) or a juxtamembrane region in the Flt3 sequence and which can inhibit the function of Flt3 was examined using HL-60 cells [Flt3 WT (wild-type) low expressing cells], EoL-1 cells [Flt3 WT (wild-type) highly expressing cells] and MV4-11 cells [Flt3/ITD highly expressing cells].

The sequences shown below were designed as siRNAs used as the nucleic acid which can inhibit the function of Flt3, and production of these sequences was entrusted to TAKARA BIO INC.

The target sequence in the ATP-binding site region is set forth in SEQ ID NO: 1. The sense sequence of siRNA1 to this target sequence is set forth in SEQ ID NO: 2, and the antisense sequence in SEQ ID NO: 3. The target sequence in the TK region is set forth in SEQ ID NO: 4. The sense sequence of siRNA2 to this target sequence is set forth in SEQ ID NO: 5, and the antisense sequence in SEQ ID NO: 6. The target sequence in the juxtamembrane region (Flt3/JMD region) is set forth in SEQ ID NO: 7. The sense sequence of siRNA3 to this target sequence is set forth in SEQ ID NO: 8, and the antisense sequence in SEQ ID NO: 9.

(2) Introduction of Gene into Each Cell

Each kind of cell selected from HL-60 cells [Flt3 WT (wild-type) low expressing cells; ATCC CCL-240], EoL-1 cells [Flt3 WT (wild-type) highly expressing cells; ECACC 94042252] and MV4-11 cells [Flt3/ITD highly expressing cells; ATCC CRL-9591] was cultured at 37° C. in an RPMI 1640 medium (manufactured by TAKARA BIO INC.) supplemented with 10% by volume fetal bovine serum (FBS) in the presence of 5% by volume $CO_2$.

Then, the cells ($2 \times 10^5$ cells/nil) were pre-cultured for 24 hours in a 6-well plate, then recovered, and suspended so as to give a density of $1.5 \times 10^5$ cells/ml in Opti-MEM (trade name, manufactured by Invitrogen), and the synthesized siRNA was added to the resulting suspension so as to give a final concentration of 200 pmol. Transfection was carried out using Oligofectamin (trade name, manufactured by Invitrogen) in an amount of 4 µl/reaction, according to an Invitrogen's protocol attached to Oligofectamin (trade name). As a control, the cells were subjected to similar operations without adding the siRNA. The unspecific influence of the siRNA was evaluated using an siRNA to a BCR/ABL chimera mRNA.

The target sequence of the BCR/ABL chimera mRNA is set forth in SEQ ID NO: 10. The sense sequence of siRNA4 to this target sequence is set forth in SEQ ID NO: 11, and the antisense sequence in SEQ ID NO: 12.

(3) Confirmation of RNA Interference

Confirmation of RNA interference of the target gene was carried out by determining change in mRNA level by a real-time RT-PCR method as shown below.

Using Oligofectamin (trade name, manufactured by Invitrogen), each kind of cell was transfected with the synthesized siRNA. After 24 hours, whole RNA was extracted from the resulting cells with TRIzol™ reagent (manufactured by Invitrogen), and the resulting product was treated with DNaseI (manufactured by TAKARA BIO INC.). The transfection, the extraction of the whole RNA and the treatment with DNaseI were carried out according to a manufacturer's protocol of the reagent used.

The real-time PCR method was carried out using a Real Time One Step RNA PCR Kit (trade name, manufactured by TAKARA BIO INC.), 100 ng of the resulting RNA as a template and a pair of primers (each 20 pmol), that is, an oligonucleotide having the nucleotide sequence of SEQ ID NO: 13 and an oligonucleotide having the nucleotide sequence of SEQ ID NO: 14. In the real-time RT-PCR method, change in fluorescence based on SYBER Green I (manufactured by TAKARA BIO INC.) was determined with Light Cycler (trade name, manufactured by Roche). The RNA level was standardized by similarly determining GAPDH mRNA with primers set forth in SEQ ID NOs: 15 and 16.

The PCR conditions were as follows: after incubation was carried out at 95° C. for 30 seconds, the reaction was carried out in 40 cycles each consisting of the reaction at 95° C. for 1 second, then at 60° C. for 10 seconds, and at 72° C. for 30 seconds.

The results of Flt3 mRNA interference by each siRNA are shown in Table 1 below. The inhibition percentage (%) of the relative mRNA expression level (Flt3 mRNA/GAPDH mRNA) changed by using the synthesized siRNA, as calculated assuming that the relative mRNA expression level (Flt3 mRNA/GAPDH mRNA) of the cells only subjected to each operation of the transfection without adding the synthesized siRNA was 100%, was shown in Table 1.

TABLE 1

| Name of Cells | siRNA1 | siRNA2 | siRNA3 | siRNA4 |
|---|---|---|---|---|
| MV4-11 (ITD mutation-highly expressing) | 65% (1.6) | 54% (1) | 65% (1) | 5% |
| EoL1 (WT-highly expressing) | 41% (1)* | 54% (1) | 63% (1) | 8% |
| HL60 (WT-low expressing) | 31% | 46% | 38% | 7% |

*Relative ratio of inhibition defining RNA interference effect in EoL1 as 1.

As shown in Table 1, it can be seen that when siRNA1 is used, Flt3 mRNA expression in the cells having ITD mutation is inhibited by 65% relative to that of the cells without using siRNA, and Flt3 mRNA expression is selectively inhibited 1.6-fold or more relative to the inhibition ratio of Flt3 mRNA expression in the cells without ITD mutation (that is, WT).

On the other hand, it was revealed that when siRNA3 was used, regardless of the presence or absence of ITD mutation, Flt3 mRNA expression in the Flt3 highly expressing cells was inhibited by 65% relative to the cells without using an siRNA, and Flt3 mRNA expression was selectively inhibited 1.6-fold or more relative to the inhibition ratio of Flt3 mRNA expression in the Flt3 low expressing cells.

When siRNA2 was used, Flt3 mRNA expression was inhibited in all cells, and the effect was around 50% relative to the cells without using an siRNA. From the foregoing, it was confirmed that the composition of the present invention can inhibit the function of Flt3.

On the other hand, in siRNA4 irrelevant to Flt3 mRNA, inhibition of Flt3 mRNA expression did not occur. Accordingly, it was confirmed that the inhibition of Flt3 mRNA expression was sequence-specific.

EXAMPLE 2

The influence of the composition of the present invention on cell growth and apoptosis was examined.

The compositions used (synthesized siRNAs 1 to 3) of the present invention was the same as in item (1) of Examples 1 above.

The cells placed in a 96-well plate at a density of $2\times10^4$ cells/well were cultured in an RPMI medium (containing 10% by volume FBS). The cells were transfected with each of the synthesized (10 nM each) siRNAs, and after 20 hours, the cell growth activity was determined with Premix WST1 reagent (trade name, manufactured by TAKARA BIO INC.). Relative growth ability (%) compared with the growth ability of the control (cells subjected to transfection without adding an siRNA) was determined. Each experiment was carried out with n=3, and the mean was determined.

The proportion of apoptosis cells in all the cells was determined with an apoptosis detection ELISA reagent (manufactured by Roche) according to its attached protocol. Each experiment was carried out with n=3, and the mean was determined. Detection of apoptosis was carried out by performing sandwich ELISA wherein the cells having the siRNA introduced therein was washed with a PBS (phosphate buffered physiological saline), to give a cell lysate from $5\times10^3$ cells, and then a cytoplasmic fraction of the cell lysate was reacted with a biotinylated anti-histone antibody and then with a peroxidase-labeled anti-DNA antibody. After the unbound antibody was washed away, an ABTS coloring reagent was added thereto and the absorbance at 405 nm was determined, and the relative frequency of apoptosis to the control (cells subjected to transfection without adding an siRNA) was shown in %.

The results of influence of the various synthesized siRNAs on the growth activity for Flt3 mRNA expressing leukemic cells are shown in Table 2.

TABLE 2

| Name of Cells | siRNA1 | siRNA2 | siRNA3 |
|---|---|---|---|
| MV4-11 (ITD mutation-highly expressing) | 56.4% (0.49) | 41.4% (0.36) | 37.5% (0.41) |
| EoL1 (WT-highly expressing) | 68.5% (0.60) | 79.7% (0.70) | 45.1% (0.50) |
| HL60 (WT-low expressing) | 116% (1)* | 115% (1) | 90.3% (1) |

*Ratio of cell-growth activation defining RNA interference effect in HL60 as 1.

As shown in Table 2, it could be confirmed that when each of siRNAs 1 to 3 was used, growth of Flt3 mRNA highly expressing cells was selectively inhibited, respectively. It was also confirmed that when siRNA3 was used, growth of Flt3 mRNA highly expressing cells was inhibited at a concentration of an IC50 (50% inhibition concentration) of 10 nM, regardless of presence or absence of ITD mutation.

It was also confirmed that in the cells of which growth was reduced to 60% or less by introducing the siRNA, 40% or more of the cells underwent apoptosis.

EXAMPLE 3

A cassette for expressing the nucleic acid which can inhibit the function of Flt3 was designed so as to have a BamHI site, loop site, RNA PolIII (RNA polymerase III) terminator site, and HindIII site, and manufactured by TAKARA BIO INC.

The sense sequence to the ATP-binding site region is set forth in SEQ ID NO: 17, and the antisense sequence in SEQ ID NO: 18. As a control, a cassette having the same GC content as in the above-mentioned siRNA was also prepared. The sense sequence is set forth in SEQ ID NO: 19, and the antisense sequence in SEQ ID NO: 20.

The sense sequence to the Flt3/ITD region is set forth in SEQ ID NO: 21, and the antisense sequence in SEQ ID NO: 22. As a control, a cassette having the same GC content as in the above-mentioned siRNA was also prepared. The sense sequence is set forth in SEQ ID NO: 23, and the antisense sequence in SEQ ID NO: 24.

The resulting synthesized DNA was heated at 90° C. for 3 minutes. Thereafter, the DNA was immediately cooled to 37° C., and the nucleic acid having the sense sequence and the nucleic acid having the corresponding antisense sequence were annealed with each other by incubation for 1 hour to prepare a cassette for expressing the nucleic acid which can inhibit the function of Flt3.

Then, a vector carrying the nucleic acid which can inhibit the function of Flt3 was constructed using pSilencer 2.1 siRNA Expression Vector Kit (trade name, Human U6 Promoter, for Hygromysin selection, manufactured by Ambion) according to a manufacturer's protocol. In other words, the above-mentioned annealed cassette was ligated with the above-mentioned pSilencer Vector by using T4 DNA ligase to give a vector carrying the nucleic acid which can inhibit the function of Flt3. The resulting vector was used to transform $E.$ $coli$ competent cells (DH5α or JM109) and cultured at 37° C. overnight on an ampicillin-containing LB medium, then transformed colonies were selected, and pSilencer plasmid was purified. The purified plasmid was digested with BamHI and HindIII, and by using the presence of the inserted fragment as an indicator, a positive clone was confirmed. The DNA in the positive clone was also analyzed with sequencing primers of the nucleotide sequence set forth in SEQ ID NO: 25 and the nucleotide sequence set forth in SEQ ID NO: 26 respectively to confirm the nucleotide sequence of the inserted fragment in the pSilencer plasmid.

EXAMPLE 4

(1) Examination of Combination with Kinase Inhibitor

The growth inhibitory activity of treatment with a combination of the composition (synthesized siRNA3) of the present invention and a kinase inhibitor on MV4-11 (ITD mutation) cells was examined. The synthesized siRNA3 used was the same as in item (1) of Example 1 above. As the kinase inhibitor, AG1295 (manufactured by CALBIOCHEM) having high specificity to ITD mutation cells was used.

(2) Transfection into Cells

In the same manner as in item (2) of Example 1 above, MV4-11 cells were cultured at 37° C. for 24 hours in a medium obtained by supplementing 10% by volume fetal bovine serum (FBS) to an RPMI 1640 medium (manufactured by TAKARA BIO INC.) (referred to hereinafter as a culture medium) in the presence of 5% by volume $CO_2$. Then, the MV4-11 cells ($1\times10^6$ cells/ml) suspended in Opti-MEM (trade name, manufactured by Invitrogen) were transferred to a cuvette (manufactured by BIO RAD; gap of 4 mm), and siRNA3 was added to the cuvette so as to give a final concentration of 1.2 μM. Then, the cuvette was set in Gene Pulser Xcell (trade name, manufactured by BIO RAD) and thereafter pulsed with electric field intensity of 650 V/cm for 25 msec. Then, the suspension of the cells in the cuvette was added to, and suspended in, a 4-fold excess volume of the culture medium and dispensed onto a 96-well plate so as to give an amount of 100 μl/well.

As a control siRNA, an siRNA having a sequence (sense sequence, SEQ ID NO: 30; antisense sequence, SEQ ID NO: 31) of C3GFP (green fluorescent protein mutant) was subjected to the same procedures as above.

(3) AG1295 Treatment 4 mM AG1295 (dissolved in DMSO) was diluted with the above-mentioned culture medium to prepare AG1295 dilutions at a concentration of 10 μM, 6 μM and 0 μM (0.25% by volume DMSO) and added so as to give an amount of 100 μl/well to the 96-well plate prepared in step (2) above and cultured at 37° C. in the presence of 5% by volume $CO_2$. Seventy-two hours after the culture was initiated, the growth activity of the cells was determined using Premix WST-1 reagent (trade name, manufactured by TAKARA BIO INC.) according to a manufacturer's protocol. Each experiment was carried out with n=6, and the mean was determined. The relative growth ratio (%) to the growth ability of the cells transfected with the control siRNA/0 μM AG1295 was determined. The results are shown in FIG. 1.

In FIG. 1, AG1295 concentration (μM) is shown on the axis of abscissas, and the relative growth ratio (%) on the axis of ordinates. The results in the case where the control siRNA was used are shown in the black bar, and the results in the case where siRNA3 was used in the white bar.

As shown in FIG. 1, it could be confirmed that the growth of MV4-11 (ITD mutation) cells was inhibited by treatment with the kinase inhibitor alone, depending on concentration, that is, the growth was inhibited by 59.8% with 3.0 μM AG1295 or by 84.3% with 5.0 μM AG41995 as compared with the cells transfected with the control siRNA/0 μM AG1295. It could be also confirmed that when siRNA3 was used alone, growth of the cells was inhibited by 83.7% as compared with the cells transfected with the control siRNA/0 μM AG1295.

However, it could surprisingly be confirmed that when siRNA3 and AG1295 were simultaneously used, growth of the cells was inhibited very highly by 94.5% with 3.0 μM AG1295 or by 99.7% with 5.0 μM AG1295, as compared with the cells transfected with the control siRNA/0 μM AG1295.

From the foregoing, it could be confirmed that either when siRNA3 was used alone or when the composition was used in combination with the receptor type kinase inhibitor such as AG1295, a very high growth inhibitory effect can be obtained.

EXAMPLE 5

(1) Cell Growth Effect of the Vector Carrying the Nucleic Acid which can Inhibit the Function of Flt3

MV4-11 cells ($2\times10^6$ cells) previously cultured in 5% by volume $CO_2$ at 37° C. were transferred to a cuvette (manufactured by BIO RAD; gap of 4 mm), and 3 μg of the vector having the Flt3/ITD region constructed in Example 3 or 3 μg of a control vector having the same GC content as in the Flt3/ITD region was added to the cuvette. Then, the cuvette was set in Gene Pulser Xcell (trade name, manufactured by BIO RAD) and then pulsed with electric field intensity of 650

V/cm for 25 msec. Then, a suspension of the cells in the cuvette was added to, and suspended in, a 4-fold excess volume of the culture medium and dispensed onto a 96-well plate in an amount of 100 μl/well, and the cells were cultured at 37° C. in the presence of 5% by volume $CO_2$. Twenty-four hours after the culture was initiated, the growth activity of the cells was determined using Premix WST-1 reagent (manufactured by TAKARA BIO INC.) according to a manufacturer's protocol attached. Each experiment was carried out with n=6, and the mean was determined. The relative growth ratio (%) for the growth inhibitory activity of the MV4-11 cells (ITD mutation highly expressing cells) as compared with the growth ability of the control was determined. The results are shown in FIG. 2.

As shown in FIG. 2, it could be confirmed that the growth of the MV4-11 (ITD mutation highly expressing) cells is inhibited by 71.4% as compared with the control. Accordingly, it could be confirmed that similar to the synthesized siRNAs in the above-mentioned Examples 1 to 4, the siRNA of which target was the Flt3/ITD region could bring about an effect of efficiently inhibiting the growth of MV4-11 which was highly expressing ITD mutation.

EXAMPLE 6

(1) Synthesis and Selection of Anti-Flt3 siRNA

The effectiveness of siRNA as the nucleic acid of which target was an ATP-binding site region, a kinase region (TK region) or a juxtamembrane region in the Flt3 sequence was examined using HL-60 cells (Flt3 WT low expressing), EoL-1 cells (Flt3 WT highly expressing) and MV4-11 cells (Flt3/ITD highly expressing). The siRNA used as the composition of the present invention was also produced by TAKARA BIO INC.

In this example, dsRNA not having a 3'-protruded structure was examined.

The target sequence in the ATP-binding site region is set forth in SEQ ID NO: 32. The sense sequence of an siRNA to this target sequence is set forth in SEQ ID NO: 33, and the antisense sequence in SEQ ID NO: 34. The target sequence in the TK region is set forth in SEQ ID NO: 35. The sense sequence of an siRNA to this target sequence is set forth in SEQ ID NO: 36, and the antisense sequence in SEQ ID NO: 37. The target sequence in the juxtamembrane region (Flt3/JMD region) is set forth in SEQ ID NO: 38. The sense sequence of an siRNA to this target sequence is set forth in SEQ ID NO: 39, and the antisense sequence in SEQ ID NO: 40.

(2) Introduction of Gene into Each Kind of Cell

Each kind of HL-60 cells, EoL-1 cells and MV4-11 cells was cultured at 37° C. for 24 hours in an RPMI 1640 medium (manufactured by TAKARA BIO INC.) supplemented with 10% by volume fetal bovine serum (FBS) in the presence of 5% by volume $CO_2$.

The cells were suspended in Opti-MEM (trade name, manufactured by Invitrogen) so as to give a density of $1.5 \times 10^6$ cells/ml, and the resulting suspension was transferred to a cuvette (manufactured by BIO RAD; gap of 4 mm), and the synthesized siRNA was added to the cuvette so as to give a final concentration of 1.2 μM.

Then, the cuvette was set in Gene Pulser Xcell (trade name, manufactured by BIO RAD) and thereafter pulsed with electric field intensity of 650 V/cm for 25 msec. Then, a suspension of the cells in the cuvette was added to, and suspended in, a 4-fold excess volume of the culture medium and dispensed onto a 96-well plate so as to give an amount of 100 μl/well.

As a control siRNA, an siRNA having a sequence (sense sequence, SEQ ID NO: 30; antisense sequence, SEQ ID NO: 31) of C3GFP (green fluorescent protein mutant) was subjected to the same procedures as above.

(3) Confirmation of RNA Interference

Confirmation of RNA interference of the target gene was carried out by determining change in mRNA level by a real-time RT-PCR method as described below. In other words, each kind of cell was transfected with the synthesized siRNA. After 17 hours, whole RNA was extracted from the resulting cells with TRIzol™ reagent (manufactured by Invitrogen). Thereafter, the resulting whole RNA was treated with DNaseI (manufactured by TAKARA BIO INC.). The transfection, the extraction of the whole RNA and the treatment with DNaseI were carried out according to a manufacturer's protocol, respectively.

Real-time PCR was carried out using a Real Time One Step RNA PCR Kit (trade name, manufactured by TAKARA BIO INC.), 100 ng of the resulting RNA as a template and a pair of primers (20 pmol each), that is, an oligonucleotide having the nucleotide sequence of SEQ ID NO: 13 and an oligonucleotide having the nucleotide sequence of SEQ ID NO: 14. In the real-time RT-PCR, change in fluorescence based on SYBER Green I (manufactured by TAKARA BIO INC.) was determined using Light Cycler (trade name, manufactured by Roche). The RNA level was standardized by similarly determining GAPDH mRNA with primers set forth in SEQ ID NO: 15 and 16.

The PCR conditions were as follows: after incubation was carried out at 95° C. for 30 seconds, the reaction was carried out in 40 cycles each consisting of the reaction at 95° C. for 1 second, then at 60° C. for 10 seconds, and at 72° C. for 30 seconds.

As a result, it could be confirmed that in the nucleic acid which can inhibit the function of Flt3, the nucleic acid not containing the TT' sequence protruded at the 3'-terminal can inhibit Flt3 mRNA expressed in cells having ITD mutation, to exhibit selective inhibition as compared with that of ITD mutation-free (that is, WT) cells.

EXAMPLE 7

(1) Influence of the Synthesized siRNA on Cell Growth

As the composition of the present invention, a cocktail containing the synthesized siRNA1, 2 and 3, or siRNA3 alone, was examined for its growth inhibitory activity on MV4-11 (ITD mutation) cells. The synthesized siRNA1, 2 and 3 used were the same as in item (1) of Example 1 above.

(2) Transfection into Cells

A medium for MV4-11 cells used was the same as in item (2) of above Example 1, and the cells were cultured at 37° C. for 24 hours in an RPMI 1640 medium (manufactured by TAKARA BIO INC.) supplemented with 10% by volume fetal bovine serum (FBS) (referred to hereinafter as the culture medium) in the presence of 5% by volume $CO_2$. Then, transfection of the cells with the synthesized siRNA3 was carried out in the following manner. MV4-11 cells ($2 \times 10^6$ cells/ml) suspended in Opti-MEM (manufactured by Invitrogen) were transferred to a cuvette (manufactured by BIO RAD; gap of 4 mm), and an siRNA cocktail prepared by combining equimolar amounts of synthesized siRNA1, 2 and 3, or siRNA3 alone, was added thereto so as to give a final concentration of 1.2 µM. Then, the cuvette was set in Gene Pulser Xcell (manufactured by BIO RAD) and thereafter pulsed with electric field intensity of 650 V/cm for 25 msec. Then, a suspension of the cells in the cuvette was added to, and suspended in, a 4-fold excess volume of the culture medium and dispensed onto a 96-well plate in an amount of 100 µl/well.

As a control siRNA, an siRNA having a sequence (sense sequence, SEQ ID NO: 30 in the Sequence Listing; antisense sequence, SEQ ID NO: 31 in the Sequence Listing) of C3GFP (green fluorescent protein mutant) was subjected to the same procedures as above.

(3) Determination of Cell Growth

The cells added in an amount of 100 µl/well on the 96-well plate prepared in item (2) above were cultured at 37° C. in the presence of 5% by volume $CO_2$. Seventy-two hours after the culture was initiated, the growth activity of the cells was determined using Premix WST-1 reagent (manufactured by TAKARA BIO INC.) according to a manufacturer's protocol. Each experiment was carried out with n=6, and the mean was determined. The relative growth ratio (%) as compared with the growth ability of the cells transfected with the control siRNA was determined. The results are shown in FIG. 3.

As shown in FIG. 3, siRNA3 alone showed growth inhibition to 46.5%, while the siRNA cocktail showed very high growth inhibition to 23.0%. From this result, it could be confirmed that siRNA3 alone can exhibit a sufficient growth inhibitory effect, and by further using a cocktail containing the siRNAs, a very high growth inhibitory effect can be obtained.

INDUSTRIAL APPLICABILITY

According to the present invention, there is provided a composition comprising a nucleic acid of which target is a region selected from the group consisting of a juxtamembrane region, a kinase region and an ATP-binding site region in human Flt3 and which can inhibit the function of Flt3, or a composition comprising a vector carrying the nucleic acid. The composition can be used in a method of selectively inhibiting growth of Flt3 highly expressing cells and/or Flt3/ITD mutation-containing cells, and inducing apoptosis of the cells. There is further provided a kit for the method. The composition of the present invention can be used as a therapeutic agent for a patient with leukemia.

SEQUENCE LISTING FREETEXT

SEQ ID NO: 1 is a partial cDNA sequence of ATP-binding site.

SEQ ID NO: 2 is designated as SEQ1-S. Nucleotides 20 and 21 are deoxyribonucleotides—other nucleotides are ribonucleotides.

SEQ ID NO: 3 is designated as SEQ1-AS. Nucleotides 20 and 21 are deoxyribonucleotides—other nucleotides are ribonucleotides.

SEQ ID NO: 4 is a partial cDNA sequence of TK domain.

SEQ ID NO: 5 is designated as SEQ2-S. Nucleotides 20 and 21 are deoxyribonucleotides—other nucleotides are ribonucleotides.

SEQ ID NO: 6 is designated as SEQ2-AS. Nucleotides 20 and 21 are deoxyribonucleotides—other nucleotides are ribonucleotides.

SEQ ID NO: 7 is a partial cDNA sequence of Flt3/ITD domain.

SEQ ID NO: 8 is designated as SEQ3-S. Nucleotides 20 and 21 are deoxyribonucleotides—other nucleotides are ribonucleotides.

SEQ ID NO: 9 is designated as SEQ3-AS. Nucleotides 20 and 21 are deoxyribonucleotides—other nucleotides are ribonucleotides.

SEQ ID NO: 10 is a partial cDNA sequence of bcr/abl chimera domain.

In SEQ ID NO: 11, nucleotides 20 and 21 are deoxyribonucleotides—other nucleotides are ribonucleotides.

In SEQ ID NO: 12, nucleotides 20 and 21 are deoxyribonucleotides—other nucleotides are ribonucleotides.

SEQ ID NO: 13 is a PCR primer Flt11F for amplifying a gene encoding Flt3.

SEQ ID NO: 14 is a PCR primer Flt12R for amplifying a gene encoding Flt3.

SEQ ID NO: 15 is a PCR primer G1 for amplifying a gene encoding GAPDH.

SEQ ID NO: 16 is a PCR primer G2 for amplifying a gene encoding GAPDH.

SEQ ID NO: 17 is an expression cassette Flt3SI1F for expressing siRNA for ATP-binding domain. The region of nucleotides 1 to 5 is BamHI restriction site—the region of nucleotides 26 to 34 is loop site—the region of nucleotides 54 to 59 is RNA polymerase III terminator.

SEQ ID NO: 18 is an expression cassette Flt3SI1R for expressing siRNA for ATP-binding domain. The region of nucleotides 1 to 5 is HindIII restriction site—the region of nucleotides 10 to 15 is RNA polymerase III terminator site—the region of nucleotides 35 to 43 is loop.

SEQ ID NO: 19 is an expression cassette Flt3CON1F for expressing control sequence. The region of nucleotides 1 to 5 is BamHI restriction site—the region of nucleotides 26 to 34 is loop site—the region of nucleotides 54 to 59 is RNA polymerase III terminator site.

SEQ ID NO: 20 is an expression cassette Flt3CON1R for expressing control sequence. The region of nucleotides 1 to 5 is HindIII restriction site—the region of nucleotides 10 to 15 is RNA polymerase III terminator site—the region of nucleotides 35 to 43 is loop.

SEQ ID NO: 21 is an expression cassette Flt3SI3F for expressing siRNA for Flt3/ITD domain. The region of nucleotides 1 to 5 is BamHI restriction site—the region of nucleotides 26 to 34 is loop site—the region of nucleotides 54 to 59 is RNA polymerase III terminator.

SEQ ID NO: 22 is an expression cassette Flt3SI3R for expressing siRNA for Flt3/ITD domain. The region of nucleotides 1 to 5 is HindIII restriction site—the region of nucleotides 10 to 15 is RNA polymerase III terminator site—the region of nucleotides 35 to 43 is loop.

SEQ ID NO: 23 is an expression cassette Flt3CON3F for expressing control sequence. The region of nucleotides 1 to 5 is BamHI restriction site—the region of nucleotides 26 to 34 is loop site—the region of nucleotides 54 to 59 is RNA polymerase III terminator site.

SEQ ID NO: 24 is an expression cassette Flt3CON3R for expressing control sequence. The region of nucleotides 1 to 5 is HindIII restriction site—the region of nucleotides 10 to 15 is RNA polymerase III terminator site—the region of nucleotides 35 to 43 is loop site.

SEQ ID NO: 25 is a 5'sequencing primer.

SEQ ID NO: 26 is a 3'sequencing primer.

SEQ ID NO: 27 is a juxtamembrane domain.
SEQ ID NO: 28 is a tyrosine kinase domain.
SEQ ID NO: 29 is an ATP-binding domain.
In SEQ ID NO: 30, nucleotides 20 and 21 are deoxyribonucleotides—other nucleotides are ribonucleotides.
In SEQ ID NO: 31, nucleotides 20 and 21 are deoxyribonucleotides—other nucleotides are ribonucleotides.
SEQ ID NO: 32 is a partial cDNA sequence of ATP-binding domain.
SEQ ID NO: 33 is an siRNA.
SEQ ID NO: 34 is an siRNA.
SEQ ID NO: 35 is a partial cDNA sequence of TK domain.
SEQ ID NO: 36 is an siRNA.
SEQ ID NO: 37 is an siRNA.
SEQ ID NO: 38 is a partial cDNA sequence of Flt3/ITD domain.
SEQ ID NO: 39 is an siRNA.
SEQ ID NO: 40 is an siRNA.

The invention claimed is:

1. A composition comprising a nucleic acid of which target is at least one region selected from the group consisting of a juxtamembrane region, a kinase region and an ATP-binding site region in human Flt3 and which can inhibit the function of Flt3, wherein said composition comprises a nucleic acid selected from the group consisting of:
   a nucleic acid wherein a nucleic acid comprising the nucleotide sequence of SEQ ID NO: 2 and a nucleic acid comprising the nucleotide sequence of SEQ ID NO: 3 are combined,
   a nucleic acid wherein a nucleic acid comprising the nucleotide sequence of SEQ ID NO: 5 and a nucleic acid comprising the nucleotide sequence of SEQ ID NO: 6 are combined,
   a nucleic acid wherein a nucleic acid comprising the nucleotide sequence of SEQ ID NO: 8 and a nucleic acid comprising the nucleotide sequence of SEQ ID NO: 9 are combined,
   a nucleic acid wherein a nucleic acid comprising the nucleotide sequence of SEQ ID NO: 33 and a nucleic acid comprising the nucleotide sequence of SEQ ID NO: 34 are combined,
   a nucleic acid wherein a nucleic acid comprising the nucleotide sequence of SEQ ID NO: 36 and a nucleic acid comprising the nucleotide sequence of SEQ ID NO: 37 are combined, and
   a nucleic acid wherein a nucleic acid comprising the nucleotide sequence of SEQ ID NO: 39 and a nucleic acid comprising the nucleotide sequence of SEQ ID NO: 40 are combined.

2. A composition comprising a vector carrying a nucleic acid of which target is at least one region selected from the group consisting of a juxtamembrane region, a kinase region and an ATP-binding site region in human Flt3 and which can inhibit the function of Flt3, wherein said composition comprises a nucleic acid selected from the group consisting of:
   a nucleic acid wherein a nucleic acid comprising the nucleotide sequence of SEQ ID NO: 2 and a nucleic acid comprising the nucleotide sequence of SEQ ID NO: 3 are combined,
   a nucleic acid wherein a nucleic acid comprising the nucleotide sequence of SEQ ID NO: 5 and a nucleic acid comprising the nucleotide sequence of SEQ ID NO: 6 are combined,
   a nucleic acid wherein a nucleic acid comprising the nucleotide sequence of SEQ ID NO: 8 and a nucleic acid comprising the nucleotide sequence of SEQ ID NO: 9 are combined,
   a nucleic acid wherein a nucleic acid comprising the nucleotide sequence of SEQ ID NO: 33 and a nucleic acid comprising the nucleotide sequence of SEQ ID NO: 34 are combined,
   a nucleic acid wherein a nucleic acid comprising the nucleotide sequence of SEQ ID NO: 36 and a nucleic acid comprising the nucleotide sequence of SEQ ID NO: 37 are combined, and
   a nucleic acid, wherein a nucleic acid comprising the nucleotide sequence of SEQ ID NO: 39 and a nucleic acid comprising the nucleotide sequence of SEQ ID NO: 40 are combined.

3. The composition according to claim 2, wherein the composition comprises a vector having, as a promoter, an RNA polymerase III promoter or an RNA polymerase II promoter.

4. The composition according to claim 3, wherein the promoter is a promoter selected from the group consisting of a U6 promoter, an H1 promoter, a tRNA promoter and a CMV promoter.

5. The composition according to claim 2, wherein the composition comprises, as a basic structure, a vector selected from an adenovirus vector, a lentivirus vector and a retrovirus vector.

6. A method of inducing apoptosis, characterized by selectively inhibiting growth of FLT3 highly expressing cells and/or FLT3/ITD mutation-containing cells with the composition as defined in claim 1, thereby inducing apoptosis of the FLT3 highly expressing cells and/or FLT3/ITD mutation-containing cells.

7. The method according to claim 6, characterized by using an agent inhibiting kinase in addition to the composition simultaneously or in a manner using one after another, to selectively inhibit growth of FLT3 highly expressing cells and/or FLT3/ITD mutation-containing cells, thereby inducing apoptosis of the FLT3 highly expressing cells and/or FLT3/ITD mutation-containing cells.

8. A kit for carrying out the method as defined in claim 6, wherein the kit comprises a composition, which contains a nucleic acid of which target is at least one region selected from the group consisting of a juxtamembrane region, a kinase region and an ATP-binding site region in human Flt3 and which can inhibit the function of Flt3.

* * * * *

```
                        SEQUENCE LISTING

<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide: A partial cDNA
      sequence of ATP-binding site

<400> SEQUENCE: 1
aaggtactag gatcaggtgc t                                          21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide: Designated as SEQ1-S
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 2
gguacuagga ucaggugcut t                                          21

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide: Designated as
      SEQ1-AS
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 3
agcaccugau ccuaguacct t                                          21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide: A partial cDNA
      sequence of TK domain

<400> SEQUENCE: 4
```
aacaggagtc tcaatccagg t                                    21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide: Designated as SEQ2-S
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 5
caggagucuc aauccaggut t                                    21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide: Designated as
      SEQ2-AS
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 6
accuggauug agacuccugt t                                    21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide: A partial cDNA
      sequence of FLT3/ITD domain

<400> SEQUENCE: 7
aatatgaata tgatctcaaa t                                    21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide: Designated as
      SEQ3-S
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 8
uaugaauaug aucucaaaut t                                    21

<210> SEQ ID NO 9

```
<211> LENGTH: 21
<212> TYPE: DNA
<213> ORGANISM: Artificial Sequence
<220> FEATURE:
<223> OTHER INFORMATION: Synthetic oligonucleotide: Designated as
      SEQ3-AS
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 9
auuugagauc auauucauau t                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide: A partial cDNA
      sequence of bcr/abl chimera domain

<400> SEQUENCE: 10
aagcagagtt caaaagcccu u                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 11
gcagaguuca aaagcccuut t                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 12
aagggcuuuu gaacucugct t                                              21

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide: PCR primer FLT11F
``` for amplifying a gene encoding FLT3

<400> SEQUENCE: 13
gcaatttagg tatgaaagcc agc                                            23

<210> SEQ ID NO 14
<211> LENGTH: 23
<212> TYPE: DNA
<213> ORGANISM: Artificial Sequence
<220> FEATURE:
<223> OTHER INFORMATION: Synthetic oligonucleotide: PCR primer FLT12R
      for amplifying a gene encoding FLT3

<400> SEQUENCE: 14
ctttcagcat tttgacggca acc                                            23

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide: PCR primer G1 for
      amplifying a gene encoding GAPDH

<400> SEQUENCE: 15
caacagcctc aagatcatca gc                                             22

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide: PCR primer G2 for
      amplifying a gene encoding GAPDH

<400> SEQUENCE: 16
ttctagacgg caggtcaggt c                                              21

<210> SEQ ID NO 17
<211> LENGTH: 64
<212> TYPE: DNA
<213> ORGANISM: Artificial Sequence
<220> FEATURE:
<223> OTHER INFORMATION: Synthetic oligonucleotide: Expression cassette
      FLT3SI1F for expressing siRNA for ATP-binding domain
<220> FEATURE:
<221> NAME/KEY: misc_feature
<222> LOCATION: (1)..(5)
<223> OTHER INFORMATION: BamHI restriction site
<220> FEATURE:
<221> NAME/KEY: misc_feature
<222> LOCATION: (26)..(34)
<223> OTHER INFORMATION: loop site
<220> FEATURE:
<221> NAME/KEY: misc_feature
<222> LOCATION: (54)..(59)
<223> OTHER INFORMATION: RNA polymerase III terminator

<400> SEQUENCE: 17
gatcccggta ctaggatcag gtgctttcaa gagaagcacc tgatcctagt accttttttg    60
gaaa                                                                 64

<210> SEQ ID NO 18
<211> LENGTH: 64
<212> TYPE: DNA
<213> ORGANISM: Artificial Sequence
<220> FEATURE:
<223> OTHER INFORMATION: Synthetic oligonucleotide: Expression cassette
      FLT3SI1R for expressing siRNA for ATP-binding domain

```
<220> FEATURE:
<221> NAME/KEY: misc_feature
<222> LOCATION: (1)..(5)
<223> OTHER INFORMATION: HindIII restriction site
<220> FEATURE:
<221> NAME/KEY: misc_feature
<222> LOCATION: (10)..(15)
<223> OTHER INFORMATION: RNA polymerase III terminator site
<220> FEATURE:
<221> NAME/KEY: misc_feature
<222> LOCATION: (35)..(43)
<223> OTHER INFORMATION: loop

<400> SEQUENCE: 18
agcttttcca aaaaggtac taggatcagg tgcttctctt gaaagcacct gatcctagta      60
ccgg                                                                  64

<210> SEQ ID NO 19
<211> LENGTH: 64
<212> TYPE: DNA
<213> ORGANISM: Artificial Sequence
<220> FEATURE:
<223> OTHER INFORMATION: Synthetic oligonucleotide: Expression cassette
      FLT3CON1F for expressing control sequence
<220> FEATURE:
<221> NAME/KEY: misc_feature
<222> LOCATION: (1)..(5)
<223> OTHER INFORMATION: BamHI restriction site
<220> FEATURE:
<221> NAME/KEY: misc_feature
<222> LOCATION: (26)..(34)
<223> OTHER INFORMATION: loop site
<220> FEATURE:
<221> NAME/KEY: misc_feature
<222> LOCATION: (54)..(59)
<223> OTHER INFORMATION: RNA polymerase III terminator site

<400> SEQUENCE: 19
gatcccggag tcgtagctgc agtatttcaa gagaatactg cagctacgac tccttttttg     60
gaaa                                                                  64

<210> SEQ ID NO 20
<211> LENGTH: 64
<212> TYPE: DNA
<213> ORGANISM: Artificial Sequence
<220> FEATURE:
<223> OTHER INFORMATION: Synthetic oligonucleotide: Expression cassette
      FLT3CON1R for expressing control sequence
<220> FEATURE:
<221> NAME/KEY: misc_feature
<222> LOCATION: (1)..(5)
<223> OTHER INFORMATION: HindIII restriction site
<220> FEATURE:
<221> NAME/KEY: misc_feature
<222> LOCATION: (10)..(15)
<223> OTHER INFORMATION: RNA polymerase III terminator site
<220> FEATURE:
<221> NAME/KEY: misc_feature
<222> LOCATION: (35)..(43)
<223> OTHER INFORMATION: loop

<400> SEQUENCE: 20
agcttttcca aaaaggagt cgtagctgca gtattctctt gaaatactgc agctacgact      60
ccgg                                                                  64

<210> SEQ ID NO 21
<211> LENGTH: 64
<212> TYPE: DNA
<213> ORGANISM: Artificial Sequence
<220> FEATURE:
<223> OTHER INFORMATION: Synthetic oligonucleotide: Expression cassette
```

```
    FLT3SI3F for expressing siRNA for FLT3/ITD domain
<220> FEATURE:
<221> NAME/KEY: misc_feature
<222> LOCATION: (1)..(5)
<223> OTHER INFORMATION: BamHI restriction site
<220> FEATURE:
<221> NAME/KEY: misc_feature
<222> LOCATION: (26)..(34)
<223> OTHER INFORMATION: loop site
<220> FEATURE:
<221> NAME/KEY: misc_feature
<222> LOCATION: (54)..(59)
<223> OTHER INFORMATION: RNA polymerase III terminator

<400> SEQUENCE: 21
gatccctatg aatatgatct caaatttcaa gagaatttga gatcatattc atattttttg     60
gaaa                                                                  64

<210> SEQ ID NO 22
<211> LENGTH: 64
<212> TYPE: DNA
<213> ORGANISM: Artificial Sequence
<220> FEATURE:
<223> OTHER INFORMATION: Synthetic oligonucleotide: Expression cassette
      FLT3SI3R for expressing siRNA for FLT3/ITD domain
<220> FEATURE:
<221> NAME/KEY: misc_feature
<222> LOCATION: (1)..(5)
<223> OTHER INFORMATION: HindIII restriction site
<220> FEATURE:
<221> NAME/KEY: misc_feature
<222> LOCATION: (10)..(15)
<223> OTHER INFORMATION: RNA polymerase III terminator site
<220> FEATURE:
<221> NAME/KEY: misc_feature
<222> LOCATION: (35)..(43)
<223> OTHER INFORMATION: loop

<400> SEQUENCE: 22
agcttttcca aaaatatga atatgatctc aaattctctt gaaatttgag atcatattca     60
tagg                                                                  64

<210> SEQ ID NO 23
<211> LENGTH: 64
<212> TYPE: DNA
<213> ORGANISM: Artificial Sequence
<220> FEATURE:
<223> OTHER INFORMATION: Synthetic oligonucleotide: Expression cassette
      FLT3CON3F for expressing control sequence
<220> FEATURE:
<221> NAME/KEY: misc_feature
<222> LOCATION: (1)..(5)
<223> OTHER INFORMATION: BamHI restriction site
<220> FEATURE:
<221> NAME/KEY: misc_feature
<222> LOCATION: (26)..(34)
<223> OTHER INFORMATION: loop site
<220> FEATURE:
<221> NAME/KEY: misc_feature
<222> LOCATION: (54)..(59)
<223> OTHER INFORMATION: RNA polymerase III terminator site

<400> SEQUENCE: 23
gatcccaata atttgcttca aagatttcaa gagaatcttt gaagcaaatt atttttttg     60 gaaa                                                                  64

<210> SEQ ID NO 24
<211> LENGTH: 64
<212> TYPE: DNA
<213> ORGANISM: Artificial Sequence
<220> FEATURE:
```

<223> OTHER INFORMATION: Synthetic oligonucleotide: Expression cassette
      FLT3CON3R for expressing control sequence
<220> FEATURE:
<221> NAME/KEY: misc_feature
<222> LOCATION: (1)..(5)
<223> OTHER INFORMATION: HindIII restriction site
<220> FEATURE:
<221> NAME/KEY: misc_feature
<222> LOCATION: (10)..(15)
<223> OTHER INFORMATION: RNA polymerase III terminator site
<220> FEATURE:
<221> NAME/KEY: misc_feature
<222> LOCATION: (35)..(43)
<223> OTHER INFORMATION: loop

<400> SEQUENCE: 24
agcttttcca aaaaaataa tttgcttcaa agattctctt gaaatctttg aagcaaatta    60
ttgg                                                                64

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide: 5' sequencing primer

<400> SEQUENCE: 25
taatacgact cactataggg                                               20

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide: 3' sequencing primer

<400> SEQUENCE: 26
aggcgattaa gttgggta                                                 18

<210> SEQ ID NO 27
<211> LENGTH: 144
<212> TYPE: DNA
<213> ORGANISM: Artificial Sequence
<220> FEATURE:
<223> OTHER INFORMATION: Synthetic oligonucleotide: Juxtamembrane domain

<400> SEQUENCE: 27
tgtcacaagt acaaaaagca atttaggtat gaaagccagc tacagatggt acaggtgacc    60
ggctcctcag ataatgagta cttctacgtt gatttcagag aatatgaata tgatctcaaa   120
tgggagtttc caagagaaaa ttta                                          144

<210> SEQ ID NO 28
<211> LENGTH: 471
<212> TYPE: DNA
<213> ORGANISM: Artificial Sequence
<220> FEATURE:
<223> OTHER INFORMATION: Synthetic oligonucleotide: Tyrosine kinase
      domain

<400> SEQUENCE: 28
acgcaacagc ttatggaatt agcaaaacag gagtctcaat ccaggttgcc gtcaaaatgc    60
tgaaagaaaa agcagacagc tctgaaagag aggcactcat gtcagaactc aagatgatga   120
cccagctggg aagccacgag aatattgtga acctgctggg ggcgtgcaca ctgtcaggac   180
caatttactt gattttttgaa tactgttgct atggtgatct tctcaactat ctaagaagta   240

```
aaagagaaaa atttcacagg acttggacag agattttcaa ggaacacaat ttcagttttt      300
accccacttt ccaatcacat ccaaattcca gcatgcctgg ttcaagagaa gttcagatac      360
acccggactc ggatcaaatc tcagggcttc atgggaattc atttcactct gaagatgaaa      420
ttgaatatga aaccaaaaa aggctggaag aagaggagga cttgaatgtg c                471
```

<210> SEQ ID NO 29
<211> LENGTH: 517
<212> TYPE: DNA
<213> ORGANISM: Artificial Sequence
<220> FEATURE:
<223> OTHER INFORMATION: Synthetic oligonucleotide: ATP-binding domain

<400> SEQUENCE: 29

```
gagtttggga aggtactagg atcaggtgct tttggaaaag tgatgaacgc aacagcttat       60
ggaattagca aacaggagt ctcaatccag gttgccgtca aaatgctgaa agaaaaagca       120
gacagctctg aaagagaggc actcatgtca gaactcaaga tgatgaccca gctgggaagc      180
cacgagaata ttgtgaacct gctgggggcg tgcacactgt caggaccaat ttacttgatt      240
tttgaatact gttgctatgg tgatcttctc aactatctaa gaagtaaaag agaaaaattt      300
cacaggactt ggacagagat tttcaaggaa cacaatttca gttttttaccc cactttccaa     360 tcacatccaa attccagcat gcctggttca agagaagttc agatacaccc ggactcggat      420
caaatctcag ggcttcatgg gaattcattt cactctgaag atgaaattga atatgaaaac      480 caaaaaggc tggaagaaga ggaggacttg aatgtgc                                517
```

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 30

```
gguuauguac aggaacgcat t                                                 21
```

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 31

```
ugcguuccug uacauaacct t                                                 21
```

<210> SEQ ID NO 32
<211> LENGTH: 19
<212> TYPE: DNA

```
<213> ORGANISM: Artificial Sequence
<220> FEATURE:
<223> OTHER INFORMATION: Synthetic oligonucleotide: A partial cDNA
      sequence of ATP-binding domain

<400> SEQUENCE: 32
ggtactagga tcaggtgct                                                    19

<210> SEQ ID NO 33
<211> LENGTH: 19
<212> TYPE: RNA
<213> ORGANISM: Artificial Sequence
<220> FEATURE:
<223> OTHER INFORMATION: Synthetic oligonucleotide: siRNA

<400> SEQUENCE: 33
gguacuagga ucaggugcu                                                    19

<210> SEQ ID NO 34
<211> LENGTH: 19
<212> TYPE: RNA
<213> ORGANISM: Artificial Sequence
<220> FEATURE:
<223> OTHER INFORMATION: Synthetic oligonucleotide: siRNA

<400> SEQUENCE: 34
agcaccugau ccuaguacc                                                    19

<210> SEQ ID NO 35
<211> LENGTH: 19
<212> TYPE: DNA
<213> ORGANISM: Artificial Sequence
<220> FEATURE:
<223> OTHER INFORMATION: Synthetic oligonucleotide: A partial cDNA
      sequence of TK domain

<400> SEQUENCE: 35
caggagtctc aatccaggt                                                    19

<210> SEQ ID NO 36
<211> LENGTH: 19
<212> TYPE: RNA
<213> ORGANISM: Artificial Sequence
<220> FEATURE:
<223> OTHER INFORMATION: Synthetic oligonucleotide: siRNA

<400> SEQUENCE: 36
caggagucuc aauccaggu                                                    19

<210> SEQ ID NO 37
<211> LENGTH: 19
<212> TYPE: RNA
<213> ORGANISM: Artificial Sequence
<220> FEATURE:
<223> OTHER INFORMATION: Synthetic oligonucleotide: siRNA

<400> SEQUENCE: 37
accuggauug agacuccug                                                    19

<210> SEQ ID NO 38
<211> LENGTH: 19
<212> TYPE: DNA
<213> ORGANISM: Artificial Sequence
<220> FEATURE:
<223> OTHER INFORMATION: Synthetic oligonucleotide: A partial cDNA
      sequence of FLT3/ITD domain

<400> SEQUENCE: 38
```

```
tatgaatatg atctcaaat                                           19

<210> SEQ ID NO 39
<211> LENGTH: 19
<212> TYPE: RNA
<213> ORGANISM: Artificial Sequence
<220> FEATURE:
<223> OTHER INFORMATION: Synthetic oligonucleotide: siRNA

<400> SEQUENCE: 39
uaugaauaug aucucaaau                                           19

<210> SEQ ID NO 40
<211> LENGTH: 19
<212> TYPE: RNA
<213> ORGANISM: Artificial Sequence
<220> FEATURE:
<223> OTHER INFORMATION: Synthetic oligonucleotide: siRNA

<400> SEQUENCE: 40
auuugagauc auauucaua                                           19
```